US012702609B2

(12) United States Patent
Harch

(10) Patent No.: US 12,702,609 B2
(45) Date of Patent: Aug. 11, 2026

(54) HYPERBARIC OXYGEN THERAPY (HBOT) CALIBRATIONS BASED ON IN-CHAMBER BRAINWAVE METRICS

(71) Applicant: Paul G. Harch, New Orleans, LA (US)

(72) Inventor: Paul G. Harch, New Orleans, LA (US)

( * ) Notice: Subject to any disclaimer, the term of this patent is extended or adjusted under 35 U.S.C. 154(b) by 0 days.

(21) Appl. No.: 18/642,243

(22) Filed: Apr. 22, 2024

(65) Prior Publication Data

US 2024/0307246 A1 Sep. 19, 2024

Related U.S. Application Data

(62) Division of application No. 16/570,938, filed on Sep. 13, 2019, now abandoned.

(Continued)

(51) Int. Cl.

| | |
|---|---|
| ***A61G 10/02*** | (2006.01) |
| ***A61M 21/00*** | (2006.01) |
| ***G05B 13/02*** | (2006.01) |

(52) U.S. Cl.

CPC ........... *A61G 10/026* (2013.01); *A61M 21/00* (2013.01); *G05B 13/027* (2013.01); *A61M 2021/0077* (2013.01); *A61M 2230/10* (2013.01)

(58) Field of Classification Search

CPC ................ A61G 10/026; A61M 21/00; A61M 2021/0077; A61M 2230/10;

(Continued)

(56) References Cited

U.S. PATENT DOCUMENTS

| | | | |
|---|---|---|---|
| 2011/0015503 A1 | 1/2011 | Joffe et al. | |
| 2011/0028827 A1 | 2/2011 | Sitaram et al. | |

(Continued)

FOREIGN PATENT DOCUMENTS

| | | |
|---|---|---|
| KR | 20190029036 A | 3/2019 |
| WO | WO 2006/032918 A1 | 3/2006 |
| WO | WO 2018110544 A1 | 6/2018 |

OTHER PUBLICATIONS

Dolmierski, R., & Maslowski, J. (1988). EEG changes under hyperbaric conditions: Spectral analysis during simulated diving. Acta Neurologica Scandinavica, 77(6), 437-439. https://doi.org/10.1111/j.1600-0404.1988.tb05936.x (Year: 1988).*

(Continued)

*Primary Examiner* — Charles A Marmor, II
*Assistant Examiner* — Marc D. Honrath
(74) *Attorney, Agent, or Firm* — Jenkins, Taylor & Hunt, P.A.

(57) ABSTRACT

Hyperbaric oxygen therapy (HBOT) settings of gas mixture and pressure are established based on electroencephalography (EEG) readings from a human within a hyperbaric chamber. Specifically, brainwave readings are affected by the HBOT process, which are used to improve the medical benefits achieved through the HBOT therapy regime, especially for treatments of cognitive disorders and neurological conditions detectable via EEG. In embodiments, HBOT settings are altered until a treated human is placed in a healing state, where cognition is enhanced. This healing state is quantitively definable through analysis of Alpha, Beta, Delta, and Theta EEG readings taken while in chamber and while outside the chamber. Once settings are determined to achieve a healing state of positive cognition, HBOT sessions can be conducted at pressure and gas mixture settings to ensure the healing state is achieved for each session. Post treatment analysis can be performed to determine EEG quantifiable improvements achieved.

11 Claims, 12 Drawing Sheets

Related U.S. Application Data

(60) Provisional application No. 62/900,287, filed on Sep. 13, 2019, provisional application No. 62/732,404, filed on Sep. 17, 2018, provisional application No. 62/730,839, filed on Sep. 13, 2018.

(58) Field of Classification Search
CPC ......... A61M 2202/0208; G05B 13/027; A61B 5/374; A61B 5/4836
See application file for complete search history.

(56) References Cited

U.S. PATENT DOCUMENTS

2013/0047988 A1* 2/2013 Delp, II .............. A61M 16/085 128/204.22
2018/0310854 A1 11/2018 Geva et al.

OTHER PUBLICATIONS

Pastena, L., & Formaggio, E. (2014). Tracking EEG changes during the exposure to hyperbaric oxygen. Clinical Neurophysiology, 126(2), 339-347. https://doi.org/10.1016/j.clinph.2014.05.013 (Year: 2014).*
Final Office Action for U.S. Appl. No. 16/570,938 dated Nov. 20, 2023.
Non-Final Office Action for U.S. Appl. No. 16/570,938 dated May 22, 2023.
Harch, Oxygen and Pressure Epigenetics: Understanding Hyperbaric Oxygen Therapy After 355 Years as the Oldest Gene Therapy Known to Man, Townsend Letter, Apr. 2018, 417, pp. 30-34.
Harch et al., "Case control study: hyperbaric oxygen treatment of mild traumatic brain injury persistent post-concussion syndrome and post-traumatic stress disorder," Medical Gas Research, vol. 7, No. 3, pp. 156-174 (2017).
Harch et al., "Subacute normobaric oxygen and hyperbaric oxygen therapy in drowning, reversal of brain volume loss: a case report," Med Gas Res. 7(2), pp. 144-149 (2017).
Harch, Paul G., "HBO Therapy in Global Cerebral Ischemia/Anoxia and Coma," K.K. Jain, Textbook of Hyperbaric Medicine, DOI 10.1007/978-3-319-47140-2_20, pp. 269-319 (2017).
Harch, Paul G., "HBO in the Management of Cerebral Palsy," K.K. Jain, Textbook of Hyperbaric Medicine, DOI 10.1007/978-3-319-47140-2_23, pp. 351-364 (2017).
Harch, Paul G., "Hyperbaric oxygen in chronic traumatic brain injury: oxygen, pressure, and gene therapy," Medical Gas Research 5:9, 4 pages (2015).
Harch, Paul G., "Hyperbaric Oxygen Therapy for Post-Concussion Syndrome: Contradictory Conclusions from a Study Mischaracterized as Sham-Controlled," J Neurotrauma 30, pp. 1995-1999 (2013).
Harch et al., "A Phase I Study of Low-Pressure Hyperbaric Oxygen Therapy for Blast-Induced Post Concussion Syndrome and Post-Traumatic Stress Disorder," Journal of Neurotrauma, 29, pp. 168-185 (2012).
Harch et al., "Low pressure hyperbaric oxygen therapy and SPECT brain imaging in the treatment of blast- induced chronic traumatic brain injury (post-concussion syndrome) and post traumatic stress disorder: a case report," Cases Journal, 2, 6538, 5 pages (2009).
Harch et al., "Interview with Dr. Paul Harch: The Application of Hyperbaric Oxygen Therapy in Chronic Neurological Conditions," Medical Veritas 2(2), pp. 637-646 (2005).
Harch PG., The Dosage of Hyperbaric Oxygen in Chronic Brain Injury. In The Proceedings of the 2nd International Symposium on Hyperbaric Oxygenation for Cerebral palsy and the Brain- Injured Child. Ed. James T. Joiner. Best Publishing Co., Flagstaff, Arizona, pp. 31-56 (2002).
Holbach et al. "Reversibility of the Chronic Post-Stroke State," Stroke, vol. 7, No. 3, pp. 296-300 (1976).
Holbach et al. EEG Analysis for Evaluating Chronic Cerebral Ischemia Treated by Hyperbaric Oxygenation and Microneurosurgery, Jour. Neurology 219, pp. 227-240 (1978).
Holbach et al. Hyperbaric Oxygenation: a Treatment in Neurosurgery, Proceedings of the Society of British Neurological Surgeons, J Neurol Neurosurg Psychiatry, Oct.;33(5)-717 (1970).
Wassmann et al. "Long term EEG analytical and neurological follow-up study in completed stroke patients after extra-intracranial vascular anastomosis," Neurological Research, vol. 6, pp. 115-117, Sep. 1984.
Barratt DM, Harch PG, Van Meter K. Decompression illness in divers: a review of the literature. Neurologist, vol. 8, No. 3: pp. 186-202. (May 2002).
Harch, Paul G., "Paul G. Harch, MD: The genetically modulated healing effects of hyperbaric oxygen therapy," Altern. Ther. Health Med. 21(1), pp. 46-55 (2015).
Harch, Paul G., "Department of Defense trials for hyperbaric oxygen and TBI: issues of study design and questionable conclusions," Letters to the Editors—Undersea Hyperb Med. 40(5), pp. 469-470 (2013).
Harch et al. Hyperbaric oxygen therapy improves spatial learning and memory in a rat model of chronic traumatic brain injury. Brain Res. Oct. 12, 2007;1174:120-9. Epub Aug. 2007.
Harch PG. Medicine that overlooks the evidence. Arch Phys Med Rehabil. Apr. 2006;87(4):592.
Harch PG, Deckoff-Jones J, Neubauer RA, "Low Pressure Hyperbaric Oxygen Therapy for Pediatric Brain Injury, A Minimal Risk Medical Treatment," PEDIATRICS, The American Academy of Pediatrics, P3R Review on Pediatrics Online, Feb. 12, 2001.
Harch PG. Late treatment of decompression illness and use of SPECT brain imaging. In Treatment of Decompression Illness, 45th Workshop of the Undersea and Hyperbaric Medical Society (eds RE Moon, PJ Sheffield). UHMS, Kensington, 203-242 (1996).
Harch PG, Van Meter KW, Neubauer RA, Gottlieb SF. Use of HMPAO SPECT for assessment of response to HBO in ischemic/hypoxic encephalopathies. In: Jain KK (ed). Textbook of hyperbaric medicine, 2nd Revised Edition. Hogrefe & Huber Publishers, Seattle WA, pp. 480-491 (1996).
Holbach et al. Superficial temporal-middle cerebral artery anastomosis for internal carotid occlusion. Acta Neurochirurgica 37, pp. 201-217 (1977).
Holbach et al., "Correlation between electroencephalographical and rCBF changes during hyperbaric oxygenation," Proc. 6th Int. Cong. On Hyperbaric Medicine, pp. 112-117 (1977).
Holbach et al. Differentiation between reversible and irreversible post-stroke changes in brain tissue: its relevance for cerebrovascular surgery. Surg. Neurol. vol. 7 (Jun. 1977).
Holbach et al. Advantage of using hyperbaric oxygenation (HO) in combination with extra-intracranial arterial bypass (EIAB) in the treatment of completed stroke. Acta. Neurochirurgica, Suppl. 28, p. 309 (1979).
Van Meter (2008) "Hyperbaric oxygen improves rate of return of spontaneous circulation after prolonged normothermic porcine cardiopulmonary arrest," Resuscitation, 78(2), pp. 200-214. Epub May 16, 2008.

* cited by examiner

Visual Depiction of A Three Variable System In Algorithmic (linear) Equation Solution 152

Sample Session Profile 210

| TREATMENT PROFILE (Patient; Condition) 212 | | | | | | |
|---|---|---|---|---|---|---|
| | | | | | | |
| | **Low** | **High** | | | | |
| Number of Sessions 215 | 20 | 40 | | | | |
| | | | | | | |
| | **Initial** | **During Treatment** | **Post Treatment** | | | |
| Impairment Level 220 | 50% | 45% | 45% | | | |
| Qualitative Assessment 225 | severe | severe with improvement | moderate | | | |
| | | | | | | |
| **HBOT Treatment Settings** | | | | | | |
| | Low | High | Low | High | Low | High |
| **Gas Mixture** 230 | X % Oxy | Y% Oxy | X % Air | Y% Air | X % GasA | Y% GasA |
| air; oxygen; oxygen-enriched air; additional gas (i.e., argon) | | | | | | |
| | Low | High | | | | |
| Pressure 235 | X Atm | Y Atm | | | | |
| | Low | High | | | | |
| 242 Calibration Duration | X | Y | | | | |
| 244 Duration at Target | 5 | 15 | | | | |
| 246 Rampdown | X | Y | | | | |
| 248 Total | 25 | 30 | | | | |
| | | | | | | |
| **BrainWave Readings** | | | | | | |
| | Low | High | **Weight** | | | |
| 252 Delta | X | Y | 2X | | | |
| 254 Theta | X | Y | 1.5 X | | | |
| 256 Alpha | X | Y | X | | | |
| 258 Beta | X | Y | X | | | |
| 260 Gamma | X | Y | .5X | | | |
| 262 Other | X | Y | 0 | | | |

FIG. 2

EEGpro

Summary of the Z-score analyses

Tables: Amplitude

EEGpro

Absolute Power ($uV^2$)

| Ch | Delta | Z-Delta | Theta | Z-Theta | Alpha | Z-Alpha | Beta | Z-Beta | hiBeta | Z-hiBeta |
|---|---|---|---|---|---|---|---|---|---|---|
| FP1 | 13.8 | -0.2 | 2.8 | -1.3 | 1.8 | -1.3 | 2.1 | -0.1 | 1.6 | 0.8 |
| FP2 | 14.7 | 0.1 | 2.7 | -1.2 | 2.8 | -1.2 | 2.1 | 0.1 | 1.5 | 0.8 |
| F7 | 10.3 | 0.2 | 2.8 | -0.8 | 2.1 | -0.8 | 2.4 | 0.6 | 3.4 | 1.8 |
| F3 | 8.1 | -0.3 | 3.1 | -1.3 | 3.8 | -0.7 | 4.2 | 0.6 | 6.8 | 0.7 |
| Fz | 11.8 | -0.1 | 3.2 | -1.6 | 3.4 | -1.0 | 3.8 | 0.2 | 4.8 | 0.6 |
| F4 | 11.1 | 0.1 | 3.8 | -1.3 | 3.7 | -0.8 | 3.7 | 0.3 | 5.4 | 0.8 |
| F8 | 24.4 | 1.8 | 3.3 | -0.3 | 3.8 | -0.7 | 2.7 | 0.5 | 4.2 | 1.3 |
| T3 | 10.4 | 1.4 | 1.8 | -0.8 | 2.8 | -0.2 | 2.8 | -0.3 | 2.3 | 0.2 |
| C3 | 7.8 | -0.3 | 2.3 | -1.6 | 7.3 | -0.8 | 4.1 | 0.1 | 3.8 | 0.1 |
| Cz | 7.8 | -0.5 | 2.8 | -2.0 | 8.7 | -0.7 | 3.3 | -0.8 | 3.8 | -0.1 |
| C4 | 8.1 | -0.2 | 2.8 | -1.5 | 6.8 | -0.5 | 3.4 | -0.1 | 3.7 | 0.1 |
| T4 | 7.1 | 1.0 | 2.7 | -0.1 | 4.8 | -0.1 | 2.8 | -0.2 | 3.4 | 0.8 |
| T5 | 14.1 | 1.8 | 3.8 | -0.6 | 6.5 | -0.4 | 1.7 | -1.0 | 2.8 | -0.3 |
| P3 | 8.8 | -0.1 | 2.2 | -1.6 | 11.3 | -0.4 | 2.4 | -0.8 | 2.8 | -0.4 |
| Pz | 6.8 | -1.0 | 2.4 | -1.8 | 8.5 | -0.7 | 1.9 | -1.4 | 2.2 | -0.8 |
| P4 | 6.8 | -0.4 | 2.4 | -1.6 | 11.8 | -0.3 | 2.4 | -0.5 | 2.8 | -0.2 |
| T6 | 6.0 | 0.2 | 1.8 | -1.2 | 8.2 | -0.4 | 1.4 | -1.2 | 1.7 | -0.4 |
| O1 | 7.8 | 0.2 | 2.1 | -1.5 | 7.8 | -0.8 | 1.5 | -1.6 | 1.8 | -0.8 |
| O2 | 7.8 | 0.2 | 2.8 | -1.6 | 6.8 | -0.8 | 1.3 | -1.7 | 1.8 | -0.8 |

Relative Power (%)

| Ch | Delta | Z-Delta | Theta | Z-Theta | Alpha | Z-Alpha | Beta | Z-Beta | hiBeta | Z-hiBeta |
|---|---|---|---|---|---|---|---|---|---|---|
| FP1 | 41.3 | 0.3 | 7.5 | -1.5 | 5.8 | -1.6 | 8.4 | 0.7 | 9.2 | 1.8 |
| FP2 | 40.3 | 0.4 | 7.1 | -1.6 | 5.3 | -1.8 | 6.0 | 0.3 | 9.0 | 1.7 |
| F7 | 33.8 | 0.6 | 8.4 | -1.2 | 7.8 | -1.3 | 7.7 | 0.7 | 11.0 | 1.6 |
| F3 | 23.1 | -0.1 | 8.3 | -1.6 | 10.8 | -0.8 | 11.5 | 1.6 | 13.6 | 1.8 |
| Fz | 28.4 | 0.6 | 8.3 | -1.8 | 8.6 | -1.2 | 9.9 | 1.1 | 12.4 | 1.9 |
| F4 | 27.8 | 0.7 | 7.6 | -1.9 | 8.2 | -1.1 | 9.5 | 0.8 | 13.4 | 1.8 |
| F8 | 46.3 | 1.3 | 7.2 | -1.7 | 4.9 | -2.3 | 6.1 | -0.7 | 7.9 | 0.4 |
| T3 | 34.7 | 1.4 | 6.1 | -1.6 | 12.6 | -0.7 | 6.6 | -0.7 | 7.8 | -0.1 |
| C3 | 20.1 | 0.2 | 5.9 | -2.3 | 18.6 | -0.4 | 10.4 | 0.6 | 8.8 | 0.7 |
| Cz | 21.1 | 0.6 | 7.1 | -2.2 | 17.8 | -0.3 | 9.6 | 0.4 | 8.6 | 1.0 |
| C4 | 21.7 | 0.5 | 6.7 | -1.9 | 17.8 | -0.4 | 8.8 | 0.2 | 8.9 | 1.3 |
| T4 | 33.6 | 0.8 | 9.1 | -0.8 | 13.4 | -0.8 | 6.6 | -0.7 | 11.2 | 0.7 |
| T5 | 38.8 | 2.0 | 7.4 | -1.1 | 18.3 | -0.7 | 4.3 | -1.8 | 5.1 | -0.8 |
| P3 | 18.3 | -0.8 | 6.9 | -2.0 | 28.5 | -0.2 | 6.6 | -0.8 | 6.4 | 0.3 |
| Pz | 17.8 | 0.4 | 7.8 | -1.7 | 27.8 | -0.2 | 5.8 | -1.0 | 5.5 | 0.7 |
| P4 | 17.3 | 0.4 | 6.9 | -1.9 | 28.4 | -0.3 | 5.8 | -0.9 | 6.8 | 0.5 |
| T6 | 23.2 | 1.4 | 6.9 | -1.1 | 24.6 | -0.1 | 5.4 | -1.0 | 6.7 | 0.3 |
| O1 | 28.5 | 1.9 | 6.7 | -1.3 | 23.3 | -0.8 | 4.8 | -1.3 | 6.1 | 0.1 |
| O2 | 27.3 | 2.0 | 6.8 | -1.4 | 23.3 | -0.8 | 4.8 | -1.4 | 5.7 | -0.1 |

FIG. 7 sLORETA Summary

EEG ID: 578157
Test Date: 2019-07-08
Age: 64.79
Gender: Male
Montage: Linked Ears
Eyes Closed

Extreme Z-scores

Delta: Z= 3.7 2 Hz BA: 40
Theta: Z= 3.4 4 Hz BA: 7
Alpha: Z= 5 11 Hz BA: 9
loBeta: Z= 3.1 15 Hz BA: 8
Beta: Z= 3.6 20 Hz BA: 9
hiBeta: Z= 4.2 33 Hz BA: 7
Gamma: Z= 3.8 35 Hz BA: 7
Alpha1: Z= 2.7 10 Hz BA: 9
Alpha2: Z= 5 11 Hz BA: 9

Percentage Deviant Voxels (1-45Hz)

<-1: 1%
<-2: 0%
<-3: 0%

>1: 47%
>2: 13%
>3: 2%

Delta (1-3Hz) Z-score: 3.7, Frequency: 2 Hz

Brain Area:
Parietal Lobe
Interior Parietal Lobule
Brodmann area 40

Function:
Somatosensory

Symptoms of Defect:
Fibromyalgia
Migraines
Slow Reading
Difficulty with Social Cues (R)
Dyscalculia
Dyslexia (L)
Agnosia (R)
Denial (R)
Letter Perception Problems (L)
Insensitive to Other's Emotional Expressions (R)
Receptive Language Problems (L)
Facial Recognition Problems
Spatial Orientation Problems (R)
Poor Social Skills (R)

Percentage Deviant Voxels Delta (1-3Hz)

<-1: 0%
<-2: 0%
<-3: 0%
>1: 85%
>2: 39%
>3: 10%

Online Information:
https://en.wikipedia.org/wiki/Brodmann_area_40
www.fmriconsulting.com/brodmann/BA40.html

Theta (4-7Hz) Z-score: 3.4, Frequency: 4 Hz

Brain Area:
Parietal Lobe
Superior Parietal Lobule
Brodmann area 7

Function:
Convergence of vision and proprioception
visio-motor coordination

Symptoms of Defect:
Easily Distracted
Poor Comprehension
Difficulty with Social Cues (R)
Dyslexia
Dyscalculia
Agnosia
Aphasia
Focus Issues
Obsession
Fibromyalgia
Impaired Spatial Perception
Decreased Tactile or Skin Sensitivity
Denial (R)
Insensitive to Others Emotional Expressions (R)

Percentage Deviant Voxels Theta (1-3Hz)

<-1: 0%
<-2: 0%
<-3: 0%
>1: 49%
>2: 12%
>3: 1%

Online Information:
https://en.wikipedia.org/wiki/Brodmann_area_7
www.fmriconsulting.com/brodmann/BA7.html

Alpha (8-12Hz) Z-score: 5, Frequency: 11 Hz

Right Left Right Pos Ant

Brain Area:
Frontal Lobe
Middle Frontal Gyrus
Brodmann area 9

Function:
Working memory
Cognitive flexibility
Planning
Inhibition
Abstract Reasoning

Symptoms of Defect:
Executive Function Problems
Concentration Problems
Impulsive
Oppositional
Anger Control Problems
Depressed
Failure to Initiate Actions
Obsessive Thoughts about Self
Multitasking Problems
Self-Esteem Problems (R)
Poor Social Skills (R)

Percentage Deviant Voxels Alpha (1-3Hz)

<-1: 6%
<-2: 0%
<-3: 0%
>1: 32%
>2: 11%
>3: 5%

Online Information:
https://en.wikipedia.org/wiki/Brodmann_area_9
www.fmriconsulting.com/brodmann/BA9.html

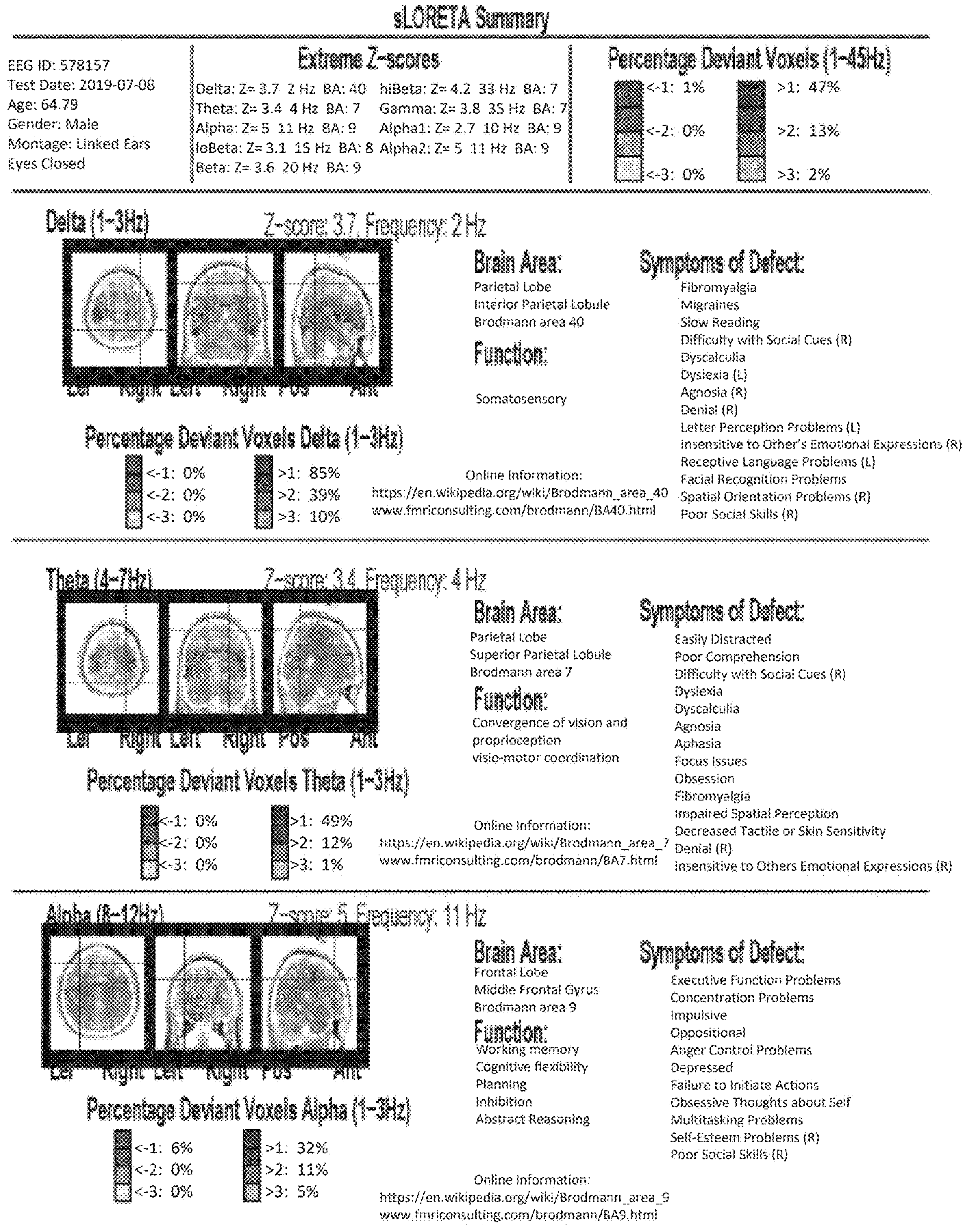

FIG. 8

Case 1
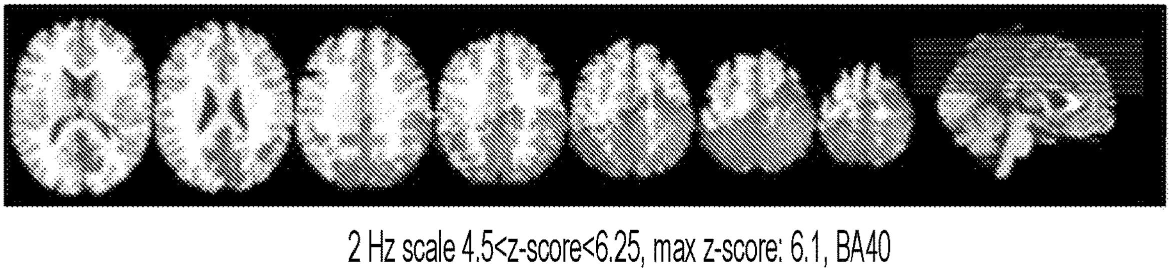
2 Hz scale 4.5<z-score<6.25, max z-score: 6.1, BA40
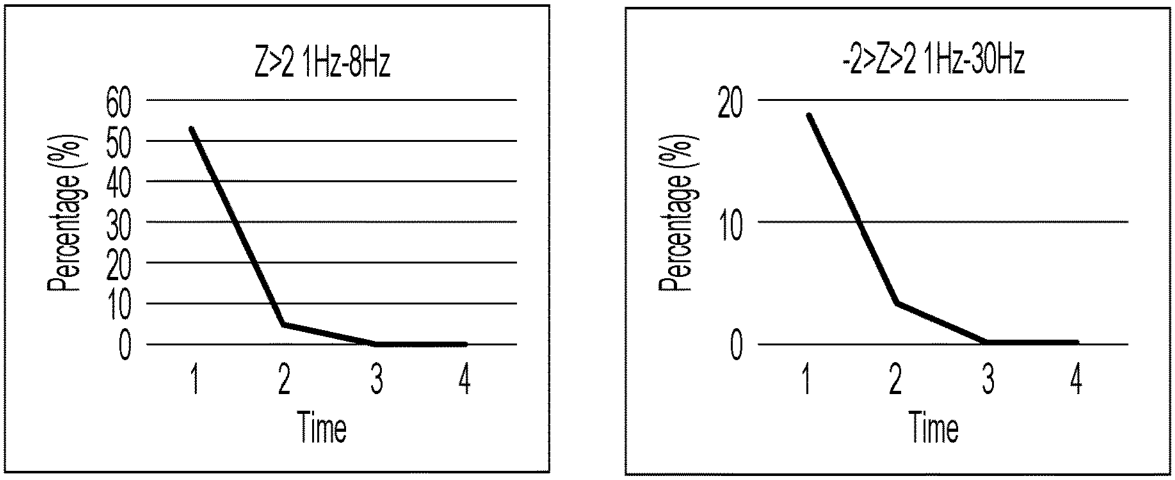
FIG. 9

HYPERBARIC OXYGEN THERAPY (HBOT) CALIBRATIONS BASED ON IN-CHAMBER BRAINWAVE METRICS

CROSS-REFERENCE TO RELATED APPLICATIONS

This Utility application is a divisional application of and claims priority to U.S. patent application Ser. No. 16/570,938 filed Sep. 13, 2019, which claims priority to U.S. Provisional Patent Application Ser. No. 62/730,839 filed Sep. 13, 2018, U.S. Provisional Patent Application Ser. No. 62/732,404 filed Sep. 17, 2018, and U.S. Provisional Patent Application Ser. No. 62/900,287 filed Sep. 13, 2019, the disclosures of each of which are incorporated herein by reference in their entirety.

BACKGROUND

The present invention relates to the field of hyperbaric medicine and electroencephalography, and more particularly to hyperbaric oxygen therapy (HBOT) calibrations based on in-chamber brainwave metrics.

Hyperbaric oxygen therapies (HBOT), when properly administered and used as part of an overall medical care plan, permits a body's natural healing process to be used to treat a wide variety of medical conditions. Conventional HBOT treatments are considered to involve as much art as science, as standards for pressure, gas mixtures, and treatment durations have not been clearly documented or mapped to different conditions. The human body is a complex system, where individual idiosyncrasies have significant effects on an optimal treatment plan or on whether HBOT is an effective treatment plan or not. Under normal circumstances, oxygen is transported throughout the body primarily by red blood cells. With HBOT, oxygen is dissolved into the plasma and thereby all of the body's fluids, the central nervous system fluids, the lymph, and the bone and can be carried to areas where circulation is diminished or blocked. In this way, extra oxygen can reach all of the damaged tissues and the body can support its own healing process. The increased oxygen greatly enhances the ability of white blood cells to kill bacteria, reduces swelling and allows new blood vessels to grow more rapidly into the affected areas. When applicable, HBOT is a simple, non-invasive and painless treatment.

Because the pressure during HBOT treatments can be significant and because treatment conditions and HBOT doses are not standardized in the industry (or even understood by many attempting to provide treatments) some patients have experienced discomfort while receiving treatment in the hyperbaric chamber; such as ear pain or a popping feeling in the ears. More severe problems include lung damage, fluid buildup or rupturing of the middle ear, sinus damage, changes in vision, oxygen poisoning, and seizures. More commonly, and especially in the case of neurological disorders, patients experience no benefit of treatment or clinically deteriorate because doses applied to non-neurological disorders, the typical wound applications in hyperbaric medicine, when rotely applied to neurological disorders are ineffective or injurious. Because of these rare, but significant negatives exhibited when treatment is improperly applied, and the more commonly mis-dosing of neurological disorders—improved dosing methods to optimize benefits while ensuring abnormalities are minimized is needed.

BRIEF DESCRIPTION OF THE SEVERAL VIEWS OF THE DRAWINGS

FIG. 2 shows a sample session profile for an HBOT treatment consistent with treatment profile in embodiments of the disclosure.

FIG. 7 shows Amplitude absolute power tables and relative power percentages across different EEG frequencies in accordance with embodiments of the disclosure.

FIG. 8 shows a sLORETA summary of different frequencies of an EEG in accordance with embodiments of the disclosure.

FIG. 9 shows scaled summary scores for different frequency ranges based on z-scores of an EEG in accordance with embodiments of the disclosure.

DETAILED DESCRIPTION

Figure 1A:
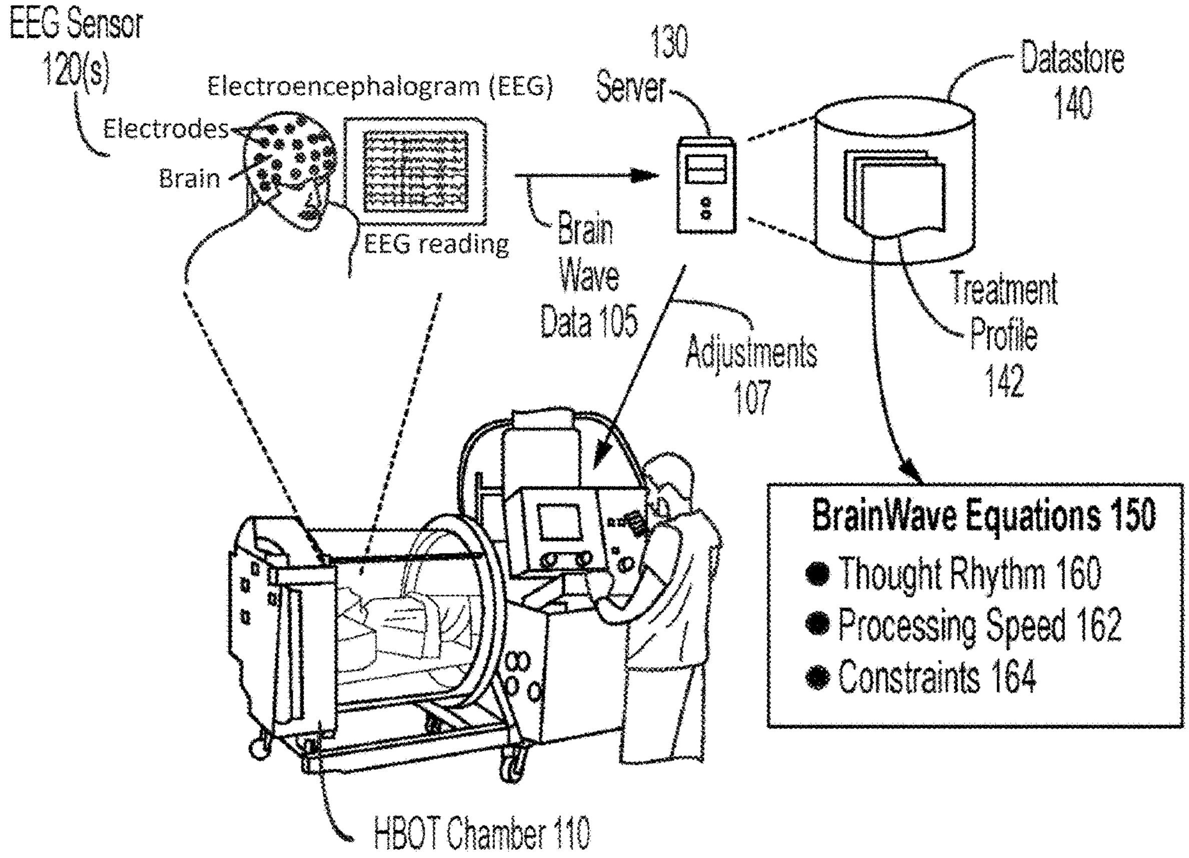
FIG. 1A shows a diagram of a system for HBOT treatments with chamber adjustments based on in-chamber brain wave readings in accordance with embodiments of the disclosure.

Embodiments of the disclosure provide for improvements in hyperbaric oxygen therapy (HBOT) systems and processes, which enable evidence-based healing of cognitive, neurological, and psychological disorders through HBOT therapy. Effectively, the disclosure determines a cognitive baseline of a patient prior to HBOT treatments, cognitive neurological, and psychological changes during HBOT treatments, and sustainable cognitive neurological, and psychological improvements resulting from treatments. Cognitive neurological, and psychological readings are used to adjust doses of the HBOT treatments themselves to calibrate the treatments for the patient's specific cognitive neurological, and psychological disorders. Simply, the patient is placed in a healing state during the HBOT treatments for a healing duration, sufficient to sustain improvements when the treatment is delivered singly or repetitively. This healing state is alternatively referred to as a neurological healing state, which represents a positive state for cognitive, psychosocial, emotional, and neural health. Achieving the healing state requires proper treatment calibration such that thought rhythm and thought speed are improved from a baseline during the healing state. Thought rhythm and thought speed can be quantified using an electroencephalography (EEG) system including EEG electrodes and an EEG processing system for EEG signals. Thought rhythm is related to Alpha, Beta, and Gamma readings or bio signals, while thought speed is related to Delta and Theta readings or bio signals. Adjustments to hyperbaric chamber settings during HBOT treatments have measurable and statistically relevant effects on Alpha, Beta, Gamma, Delta, and Theta readings. Assuming a quantification of these readings is expressed as a formula (such as a linear algebraic formula with defined variables for the different signals), a mathematical inequality, multi-variable system results, which can be solved for a proper healing state. The same healing state, which is sustainable for a healing duration, can also be achieved intuitively through manual adjustments-especially those made by a HBOT specialist. Regardless of how the system achieves a healing state, a quantifiable improvement (such as one based on percentages) of cognitive, neurological, and psychological function while in an HBOT chamber is established. Positive effects of being placed in the "heightened cognitive neurological, and psychological state" when inside the HBOT chamber are retained after HBOT treatments, which is why the disclosure refers to the calibrated, person-specific settings as establishing a healing state-synonymous with the heightened cognitive neurological, and psychological state or HBOT induced improved state of cognition, emotional well-being, psychological wellbeing, or neural well-being.

Cutting edge research and studies by the inventor are beginning to show the early results to indicate that earlier studies related to cognitive neurological, and psychological HBOT treatments were flawed. The reasoning for such flawed results is believed to be the direct result of improper dosing, a misunderstanding of the bioactivity of hydrostatic pressure separate from the bioactivity of increased oxygen, and improper monitoring of cognitive neurological, and psychological functions and changes during pressurization within a chamber to ensure the proper doses and treatment duration is established to maximize benefits. In simplest terms, past studies have simply misapplied treatment parameters, which resulted in less than optimal results, and which has also resulted in a mistaken belief that HBOT treatments were a dead end with regard to cognitive neurological, and psychological treatments. Simply stated, there was no obvious, known, or attempted way to consistently treat patients via HBOT that produced statistically relevant improvement results to justify pursing this course of treatment. This disclosure changes that assumption and provides a mechanism reliant upon intra-chamber brainwave readings to ensure HBOT treatments improve cognition neurological, and psychological function in patients.

The inventor is a pioneer of HBOT treatments, who has been involved in numerous significant publications and advancements in the field. The disclosure's dynamic treatment adjustments based on brain activity are built upon this volume of previous work, which is useful as general information. The following publications are incorporated by reference in their entirety as they provide some baseline of the knowledge known in the field, which is able to be adapted and modified in light of the disclosures/innovations (i.e., shows enabling embodiments and knowledge for which the present disclosure is compatible such that one of ordinary skill armed with the disclosure's innovative, non-intuitive, industry contradicting teachings may understand the scope and applicability of the disclosure's teachings).

1) HARCH P G. Oxygen And Pressure Epigenetics: Understanding Hyperbaric Oxygen Therapy After 355 Years As The Oldest Gene Therapy Known To Man. The Townsend Letter, April, 2018; 417: 30-34.

2) HARCH P G, Andrews S R, Fogarty E F, Lucarinij, Van Meter K W. Case Control Study: Hyperbaric Oxygen Treatment Of Mild Traumatic Brain Injury Persistent Post-Concussion Syndrome And Post-Traumatic Stress Disorder. Med Gas Res. 2017; 7(3):156-174.

3) HARCH P G, Fogarty E F. Subacute Normobaric Oxygen And Hyperbaric Oxygen Therapy In Drowning, Reversal Of Volume Loss.: A Case Report. Med Gas Res. 2017; 7(2):144-149.

4) HARCH P G. HBO Therapy In Global Cerebral Ischemia/Anoxia And Coma, Chapter 20. In: Jain K K (Ed). Textbook Of Hyperbaric Medicine, 6th Revised Edition. Springer International Publishing, Cham, Switzerland, 2017. pps. 269-319. (Major Revision And Update Of Previous Edition).

5) HARCH PG. HBO In The Management Of Cerebral Palsy, Chapter 23. In: Jain Kk (Ed). Textbook Of Hyperbaric Medicine, 6th Revised Edition. Springer International Publishing, Cham, Switzerland, 2017. Pps. 351-364. (Major Revision And Update Of Previous Edition).

6) HARCH, P G AND MCCULLOUGH, V E. The Oxygen Revolution: Third Edition. Hyperbaric Oxygen Therapy: Breakthrough Gene Therapy For Traumatic Brain Injury & Other Disorders. Hatherleigh Press, New York, 2016.

7) HARCH, PG. Hyperbaric Oxygen In Chronic Traumatic Brain Injury: Oxygen, Pressure, And Gene Therapy. Medical Gas Research.2015, 5:9. Doi: 10.1186/S13618-015-0030-6 Uri: Http://Www.Medicalgasresearch.ConContent/5/1/9

8) HARCH, PG. Paul G. Harch, Md: The Genetically Modulated Healing Effects of Hyperbaric Oxygen Therapy. Altern. Ther. Health. Med. 2015; 21(1):46-55.

9) HARCH, PAUL G. Hyperbaric Oxygen Therapy For Post-Concussion Syndrome: Contradictory Conclusions From A Study Mischaracterized As Sham-Controlled. JOURNAL OF NEUROTRAUMA, 2013; 30:1995-1999.

10) HARCH, P. G. Department Of Defense Trials For Hyperbaric Oxygen And Tbi: Issues Of Study Design And Questionable Conclusions. Undersea Hyper Med 2013; 40(5):469-70.

11) Harch, P G, Andrews. S A, Fogarty, E F, Amen, D A, et al., 2011. A Phase I Study Of Low Pressure Hyperbaric Oxygen Therapy For Blast-Induced Post Concussion Syndrome And Post Traumatic Stress Disorder. Journal Of Neurotrauma, Epub Ahead Of Print, Nov. 22, 2011: Ktp:/Iwww.1ieberton1ine.Ccmjdoi/Pdfph:S/L0.1089/Nev..201 1.L 895. 2012, 29(1):168-185.

12) Paul G. Harch, M. D. and Virginia Mccullough. The Oxygen Revolution, New Revised Edition. Hatherleigh Press, N.Y., Oct. 29, 2010.

13) Harch, P. G., Fogarty, E. F., Staab, P. K., And Van Meter, K. (2009). Low Pressure Hyperbaric Oxygen Therapy And Spect Brain Imaging In The Treatment Of Blast-Induced Chronic Traumatic Brain Injury (Post-Concussion Syndrome) And Post Traumatic Stress Disorder: A Case Report. Cases Journal, 2, 6538. Doi: 10.4076/1757-1626-2-6538http://Casesjournal.Con-Cases Journal/Artic1e/View/6538

14) Harch P G, Neubauer R A, Uszler J M, James P B. Appendix: Diagnostic Imaging and HBO Therapy, Chapter 44. In: Jain K K (ed). Textbook of Hyperbaric Medicine, 5$^{th}$ Revised Edition. Hogrefe & Huber Publishers, Seattle WA, 2009. pps. 505-520. (Moderate Revision and Update).

15) Van Meter K, Sheps S, Kriedt F, Moises J, Barratt D, Murphy-Lavoie H, Harch P G, Bazan N. Hyperbaric oxygen improves rate of return of spontaneous circulation after prolonged normothermic porcine cardiopulmonary arrest. Resuscitation, 2008 August; 78(2):200-14. Epub 2008 May 16. May 15, 2008.
16) Harch P G, Kriedt C, Van Meter K W, Sutherland R J. Hyperbaric oxygen therapy improves spatial learning and memory in a rat model of chronic traumatic brain injury. Brain Res. 2007 Oct. 12; 1174:120-9. Epub 2007 August
17) Paul G. Harch, M. D. and Virginia McCullough. The Oxygen Revolution. Hatherleigh Press, New York, Apr. 24, 2007.
18) Harch P G. Medicine that overlooks the evidence. Arch Phys Med Rehabil. 2006 April; 87(4):592-3.
19) Harch P G, Small T. Interview with Dr. Paul Harch: The Application of Hyperbaric Oxygen Therapy in Chronic Neurological Conditions. Medical Veritas, 2005; 2(2):637-46.
20) Neubauer V, Neubauer R A, Harch P G. HBO in the Management of Cerebral Palsy, Chapter 21. In: Jain K K (ed). Textbook of Hyperbaric Medicine, 4$^{th}$ Revised Edition. Hogrefe & Huber Publishers, Seattle WA, 2004. (New Chapter).
21) Harch P G. The Dosage of Hyperbaric Oxygen in Chronic Brain Injury. In The Proceedings of the 2$^{nd}$ International Symposium on Hyperbaric Oxygenation for Cerebral palsy and the Brain-Injured Child. Ed. James T. Joiner. Best Publishing Co., Flagstaff, Arizona, 2002, pp. 31-56.
22) Barrett D M, Harch P G, Van Meter K. Decompression illness in divers: a review of the literature. Neurologist. 2002 May; 8(3):186-202.
23) Harch P G, Deckoff-Jones J, Neubauer R A Low Pressure Hyperbaric Oxygen Therapy for Pediatric Brain Injury, A Minimal Risk Medical Treatment, PEDIATRICS, The American Academy of Pediatrics, P3R Review on Pediatrics Online, Feb. 12, 2001.
24) Harch P G, Neubauer R A. Hyperbaric Oxygen Therapy in Global Cerebral Ischemia/Anoxia and Coma. In: Jain K K (ed). Textbook of Hyperbaric Medicine, 3rd Revised Edition. Hogrefe & Huber Publishers, Seattle WA, 1999.
25) Harch P G, Neubauer R A, Uszler J M, James P B, Maxfield W. Functional Imaging. In: Jain K K (ed). Textbook of Hyperbaric Medicine, 3rd Revised Edition. Hogrefe & Huber Publishers, Seattle WA, 1999.
26) Van Meter K, Weiss L, Harch P G. Hyperbaric Oxygen in Emergency Medicine. In: Jain K K (ed). Textbook of Hyperbaric Medicine, 3rd Revised Edition. Hogrefe & Huber Publishers, Seattle, W A 1999.
27) Harch P G. Late treatment of decompression illness and use of SPECT brain imaging. In Treatment of Decompression Illness, 45th Workshop of the Undersea and Hyperbaric Medical Society (eds RE Moon, P J Sheffield). UHMS, Kensington, 1996, 203-242.
28) Harch P G, Van Meter K W, Neubauer R A, Gottlieb S F. Use of HMPAO SPECT for assessment of response to HBO in ischemic/hypoxic encephalopathies. In: Jain K K (ed). Textbook of hyperbaric medicine, 2nd Revised Edition. Hogrefe & Huber Publishers, Seattle WA, 1996, pp 480-491.
29) Van Meter K, Harch P, Gottlieb S. Use of hyperbaric oxygen in cardiopulmonary resuscitation (CPR). In: Jain K K (ed). Textbook of hyperbaric medicine, 2nd Revised Edition. Hogrefe & Huber Publishers, Seattle WA, 1996, pp 492-495.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Computer program code for carrying out operations for aspects of the present invention may be written in any combination of one or more programming languages, including an object-oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

FIG. 1A shows a diagram of a system for HBOT treatments with chamber adjustments based on in-chamber brain wave readings in accordance with embodiments of the disclosure. Specifically, a patient, especially one suffering from cognitive, neurological, emotional, or psychological challenges, is treated inside HBOT chamber 110. When in the chamber 110, a series of brain wave sensors 120 are connected, which permit recordings of electrical activity while receiving HBOT treatments. Data 105 from the sensors are conveyed to a server 130 or other computer, which processes this information to establish a preferred treatment profile 142. The treatment profile 142 is stored in the datastore 140 along with related information. Generally, a treatment profile 142 establishes a protocol (i.e., Harch protocol) for treatment of a specific ailment. While in the chamber 110, pressure, gas composition, and duration of a session are able to be adjusted. These adjustments effectuate changes in brain wave data 105. Effectively, an adjustment 107 responsive system is established in FIG. 1A that is inclusive of reactive brainwave data 105, where reactivity of brainwave data 105 assumes that data 105 is obtained for a patient inside the chamber 110 subject to the adjustments 107.

Figure 1B:
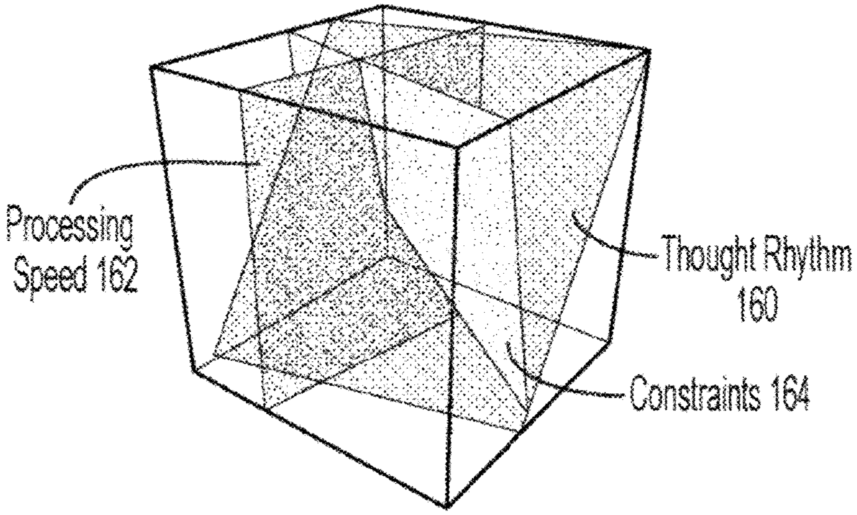
FIG. 1B shows a mathematical model for yielding solutions to optimize HBOT treatments from brainwave metrics in accordance with an embodiment of the disclosure.

More specifically, a treatment profile 142 can establish settings for adjustments 107 based on brain wave data 105 referred to as brainwave equations 150. Although numerous equations 150 are viable for purposes of this disclosure focus has been placed on those indicative of thought rhythm 160, processing speed 162, and physiological constraints 164. From an algorithmic perspective, thought rhythm 160 equations have variables for Alpha, Beta and/or Gamma values; processing speed 162 equations have variables for Theta and/or Delta values; and, constraints 164 have variables for patient specific adjustments, such as HBOT duration, gas composition, and pressure. The variables are interrelated in practice, as adjustments 107 effectuate variable changes to Alpha, Beta, Gamma, Theta, and Delta values of a patient undergoing treatment. Embodiments of the disclosure have established linear relationships between these three equations, which results in a three variable system subject to a linear equation solution 152, as depicted in FIG. 1B. That is, assuming a three-axis system, solutions to optimize the interrelated values exist, as depicted by the overlap of the planes representing thought rhythm 160, processing speed 162, and constraints 164.

Although statistically relevant and mathematically expressible optimization solutions are possible (as represented herein), it should be understood that these depictions (FIG. 1B) represent an intentional oversimplification of the problem space. Different individuals and groupings of individuals have divergent reactions to HBOT therapies. Some patients are simply more sensitive to pressure, gas composition, and duration than others during HBOT treatments due in part to physiological deltas inherent between human beings. However, averages and trends generally applicable to human groups exist, from which generalized equations modeling HBOT treatment/brainwave dynamics are constructible. In practice, manually performed adjustments 107 by trained medical specialists having real-time access to brainwave data 105 are able to inherently optimize HBOT settings better than existent rote based formulas (and automated processes given today's state of the art). Illustrative examples of data to which real-time (or near real time access) is beneficial are depicted by FIG. 4A-FIG. 9, which are elaborated upon herein. The data expressions are not intended to be comprehensive, but are instead illustrative of the types of data from which experts are able to make adjustments 107, as understandable by one of ordinary skill in the field. The above being true at present it should be understood that as with any quantifiable and repeatable process, improvements are anticipated in modeling and the equations over time, such that with increased data accuracy and precision of the model's computer-driven optimizations and automated processes are expected to improve. At present, consistent trends and statistically viable models have evolved over the course of approximately seventy patients for which preliminary tests are used to establish this disclosure. It should be understood that plainer expressions for thought rhythm 160, processing speed 162, and constraints 164 may be expressed as non-linear equations in other models, which will still yield mathematical solutions, which is the point of expressions depicted in FIG. 1B. Accordingly, the disclosure is not limited to any specific number of axis or formula types as can be readily understood by those of skill. In contemplated embodiments, for example, artificial intelligence systems, such as Hidden Markov Model (HMM) based neural networks heuristically trained, using large sets of patient data, will yield automated solutions to the problem space having greater accuracy and precision than more simplistic (and less accurate/precise) equation based models, such as those depicted in FIG. 1B.

Regardless of specific model and methodology utilized, for any given patient, a treatment profile 142 is able to be established that correlates adjustments 107 to brainwave data 105 to achieve a healing state of heightened cognitive neurological, emotional, and/or psychological functioning for a healing duration, while a patient is in the HBOT chamber 110. The improvements are a direct result of calibrating the adjustments 107 for specific brainwave values (150) along multiple different dimensions (160, 162, and 164). More specifically, by interpreting different EEG readings indicative of functional improvements in cognition, neurological health, emotional well-being, and/or psychological function (thought rhythm 160 and processing speed 162) a reasonable quantified enhanced brain activity or improved cognitive state is established.

Unlike conventional HBOT treatments, the brain-wave based ones are quantified to improve cognitive, neurological, and psychological functioning. Specifically, the in-treatment adjustments provide a heightened healing period, which studies (See Appendixes of relied upon Provisional converted herein) show provide post-treatment benefits. That is, by being in a healing period for which a patient's cognitive neurological, and psychological health is expressly monitored and advantageously adjusted, the brain's ability to think (cognition) and neurologically and psychologically function as determined from brain waves (EEG read electrical signals) improves directly and then subsequently with treatment at the determined best dose. The targets of pressure and oxygen for such improvements can vary from person to person since each person is idiosyncratic and their brain injury or disorder renders them even more idiosyncratic and individual. These settings are therefore dynamic. The settings, however, are relatively stable for a given patient across multiple treatment sessions. Thus, a patent may only need to be connected to EEG sensors 120 for a first treatment to establish a proper treatment profile. In other embodiments, EEG sensor readings 120 can be taken during the treatment regime to optimize and adjust parameters (107) as necessary.

Conventional attempts at cognitive, neurological, emotional, and psychological improvement through HBOT were largely inconsistent from an evidence/improvement perspective due in part to a lack of focus on achieving a target state of improved cognition, neurological health, emotional well-being, and/or psychological function for a treatment duration or a patient-specific dose of hyperbaric therapy. Conversely, the disclosure has shown clear and consistent improvements in cognitive state through proper application of a set of HBOT sessions per a treatment profile 142, which may be individually tailored. It is anticipated that the EEG sensors 120 are necessary to achieve patient-specific cognitive, neurological, emotional, and psychological improvements (at least optimal ones), as results of HBOT treatments vary significantly from patient to patient (when correlated against brain wave data 105). Further, patient reaction to HBOT treatments has varied by patient sensitivity so in-treatment readings (data 105) is believed to be necessary to achieve optimal improvement results. In short, one cannot receive the same cognitive neurological, emotional, and psychological benefits generally without conducting in-chamber (110) brainwave readings (105). It is possible, however, that extensive data (140) obtained over time while monitoring many patients may provide aggregate data to establish thresholds able to be loosely followed by different categories of patients without reading in-chamber brain wave data 105. Such lose guidelines will be non-optimal compared to tailored ones, but using conventional information are not possible today. That is, even the establishment of such guidelines requires extensive patient specific data correlated against cognitive, neurological, emotional, and psychological levels, which is not existent today, yet which could viably result from use of the disclosed system.

Figure 1C:
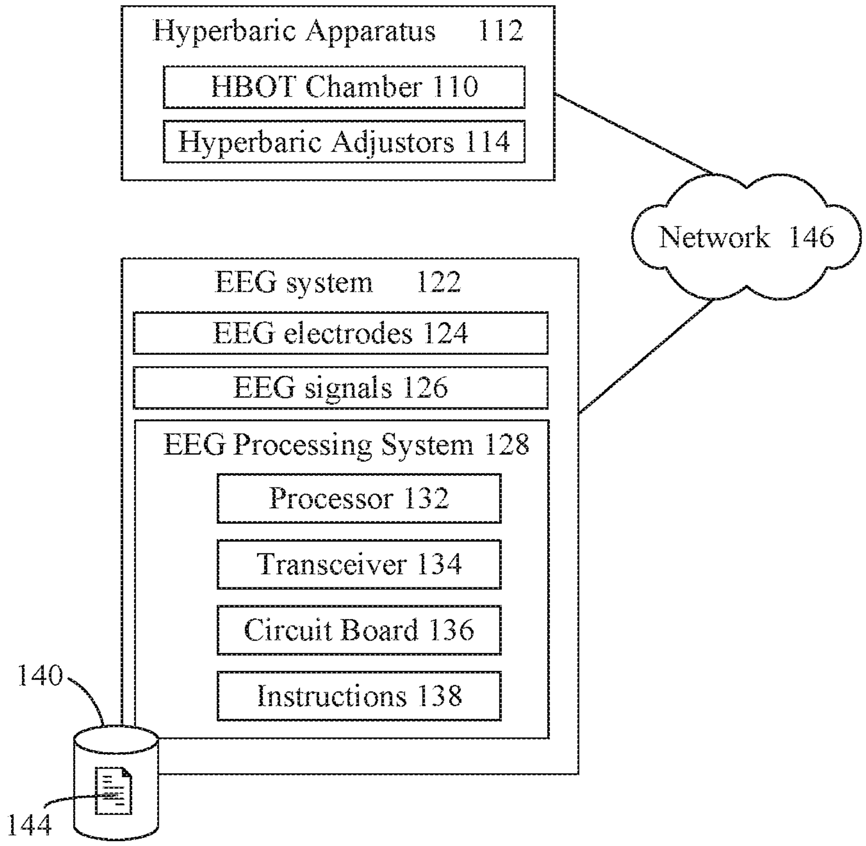
FIG. 1C depicts the system of FIG. 1A as a block diagram showing network connectively and additional components.

FIG. 1C depicts the system of FIG. 1A as a block diagram. Specifically, FIG. 1C shows a hyperbaric apparatus 112 communicatively linked to an EEG system 122 by network 146. The hyperbaric apparatus 112 includes the HBOT chamber 110 as well as hyperbaric adjustors 114, which are apparatus components to which adjustments 107 are made. The EEG system 112 includes EEG electrodes 124, EEG signals 126, and an EEG processing system 128. One or more datastores 140 persists (i.e. stores) information, such as data and values 144 related to the treatment profile 142.

The hyperbaric apparatus 112 is an adjustable device designed to enable patients to undergo HBOT treatments. HBOT treatments often involve developing high blood oxygen concentrations (while in the healing state) during HBOT based on applications of Boyle's Law, Dalton's Law, Henry's Law, Graham's Law and other gas laws including Gay Lussac's Law, Charles' Law, Pascal's Law, and the General Gas Law.

The hyperbaric chamber 110 is an enclosure in which one or more patients are exposed to pressure higher than atmospheric pressure. A chamber 110 designed for a single individual is typically referred to as a monoplace chamber, which may be problematic for some claustrophobic patients. Multiplace chambers are designed for treating multiple patients at once; such as permitting 18 patients to receive concurrent treatments during which these patients may sit in a chair or recline. Each patient in chamber 110 is also exposed to a gas mixture, which is controllable by a treating physician. The walls of a hyperbaric chamber 110 are usually made of steel, but other materials are used in some circumstances. For example, soft chambers (mild hyperbaric oxygen therapy mHBOT) exist, which are usually purchased by private individuals for their portability, compact size, and ease of use. The thickness of the walls of some hyperbaric chambers may create a Faraday effect, which causes electromagnetic insulation, blocking any electromagnetic signal. Fortunately, hyperbaric chamber 110 will generally include one or more windows (with 40 mm thickness methacrylate for example) that allow bidirectional wireless communication. Thus, communications of EEG signals 126 to/from the HBOT Chamber 110 is generally not problematic. Regarding the atmosphere in which the electronic system will be working, the pressure inside the chamber is generally obtained by inflating an interior of the chamber greater than that of the ambient environment from pressures slightly greater than what is found at sea level to up to 1.3 Absolute Atmosphere (ATA), or 4 pounds per square inch (PSI) above ambient atmospheric pressure for mHBOT chambers. Commercial, portable non-mild HBOT chambers permit pressures up to 3 ATA or 44.1 PSI absolute. Heavier chambers exist that are designed to be pressurized up to 6 ATAs. Although typical HBOT treatments have patients breathe 100% oxygen (creating oxygen-rich, nitrogen-poor blood), other mixtures such as hyperbaric air (21% oxygen; 78% nitrogen; 1% trace gasses, primarily argon), nitrox (a mixture of oxygen and air, which utilizes more than 2% oxygen), and other mixtures can be used. Different advantageous mixtures can be tailored for specific conditions being treated. As evidence and records accumulate through specific case studies and HBOT treatment applications, best in breed mixtures will continue to group for specific conditions and pressure settings permitting further optimizations.

Hyperbaric adjustors 114 are components of the apparatus 112 that change environmental conditions. Adjustors 114 include pressure adjustors that permits pressure in the chamber 110 to be upwardly and downwardly adjusted within the effective operating range of the chamber 110. Adjustors 114 also include gas composition adjustor that changes which of a set of available gases and gas concentrations a patient breathes while in the chamber.

The EEG system 122 is one that measures voltage fluctuations resulting from ionic current within the neurons of the brain or that records a brain's electrical activity over a period of time. Although EEG systems generally refer to only those systems that directly measure the brain's electrical activity, the disclosure intentionally utilizes an expansive definition that includes systems that measure brain electrical activity through indirect markers. Thus, EEG system 122, as used herein, includes systems that record changes in blood flow (e.g., Single-photon emission computed tomography (SPECT) type systems, magnetic, and/or Functional magnetic resonance imaging fMRI) as well as methods dependent on metabolic activity (e.g., Positron-emission tomography (PET) and Functional Near-Infrared Spectroscopy (NIRS)). Conventional EEG systems 122 that measure electrical activity directly are beneficial in some embodiments due to lower cost and the ease with which the sensors and readings are implemented while a patient is within the chamber 110. Further, the speed and resolution of conventional EEG techniques are beneficial in embodiments.

EEG electrodes 124 include passive, active, dry, and sponge electrodes. Passive and active electrodes are often categorized as gel electrodes, which sometimes permit recordation over a wide frequency range and permit high quality data. Passive electrodes are usually made of silver/silver chloride (Ag—AgCl) and may be applied to the scalp using a conductive gel or paste, usually after preparing the scalp area by light abrasion to reduce electrode-scalp impedance. Active electrodes include circuits integrated in a housing of the sensors that permit recordings at high transition resistances (up to 500 kOhm) and minimize ambient noise, interference due to electrical effects and artifacts due to cable movement thanks to built-in active shielding. Dry electrodes are tailored for ease of application and optimum contact between the electrode and scalp in order to remove the necessity of electrode gel. With the flexible cap and the mushroom-shaped electrodes it is easy to establish good electrode contacts. The exceptional feature, however, is the adjustable electrode length, that allows adapting the cap to any head geometry—even while a test subject is wearing the cap. Sponge electrodes include passive Ag/AgCl electrodes that are held in place with a durable and flexible net. Due to the gel-free application it allows for rapid preparation and high recording flexibility, which is advantageous e.g. in time-restricted EEG recording situations.

EEG signals 126 are a subset of signals acquired from the human body and specifically acquired by the EEG system 122 via the EEG electrodes 124. In embodiments, EEG electrode 124 derived signals can be aggregated or supplemented with other bio signals to refine the EEG signals 126 processed by system 128. As used herein, EEG signals 126 include or incorporate brainwave data 105 of a patient equipped with EEG sensors 120 (or EEG electrodes 124). Values used to determine the thought rhythm 160 and the processing speed 162 are obtained or derived from the EEG signals 126. In embodiments, the EEG signals 126 can be ones indicative of voltage fluctuations resulting from ionic current within neurons of a brain of the patient.

The EEG processing system 128 is a system for determining, analyzing, and presenting at least Alpha, Beta, Gamma, Delta, and Theta values of the patient. That is, the EEG processing system 128 obtains and analyses EEG signals 126. The EEG processing system 128 can include a microprocessor 132, a transceiver 134, one or more circuit boards 136, and programmatic instructions 138, which the processor 132 executes. Reports and data represented by FIG. 4A-FIG. 9 are generated, produced, and presented utilizing the EEG processing system 128 and components thereof.

As used herein, presented data store 140 is a physical or virtual storage space configured to store digital information. Data store 140 can be physically implemented within any type of hardware including, but not limited to, a magnetic disk, an optical disk, a semiconductor memory, a digitally encoded plastic memory, a holographic memory, or any other recording medium. Data store 140 can be a stand-alone storage unit as well as a storage unit formed from a plurality of physical devices. Additionally, information can be stored within data store 140 in a variety of manners. For example, information can be stored within a database structure or can be stored within one or more files of a file storage system, where each file may or may not be indexed for information searching purposes. Further, data store 140 can utilize one or more encryption mechanisms to protect stored information from unauthorized access.

Network 146 can include any hardware/software/and firmware necessary to convey data encoded within carrier waves. Generally, network 146 will be a personal area network (PAN) utilizing a protocol such as BLUETOOTH, ZIGBEE, WIFI, or the equivalent; yet network 146 is not limited in this regard. Data can be contained within analog or digital signals and conveyed though data (or voice) channels. Network 146 can include local components and data pathways necessary for communications to be exchanged among computing device components and between integrated device components and peripheral devices. Network 146 can also include network equipment, such as routers, data lines, hubs, and intermediary servers which together form a data network, such as the Internet. Network 146 can also include circuit-based communication components and mobile communication components, such as telephony switches, modems, cellular communication towers, and the like. Network 146 can include line based and/or wireless communication pathways.

FIG. 2 shows a sample session profile 210 for an HBOT treatment consistent with treatment profile 142 in embodiments of the disclosure. The profile 210 represents data 144 related to the profile 142 in embodiments. Profile 210 is shown for illustrative purposes only and not all elements of profile 210 are needed for each patient and additional element may be useful for specific conditions and patients.

As shown, the session profile 210 is tailored for a specific individual having a specific condition 212 being treated. Different people and conditions can affect the HBOT treatment settings. A typical course of 40 treatments can be part of a treatment profile 142, where adjustments can be made session to session in one embodiment. That is, different adjustments (107) can be made for early ones of the forty sessions, which results in later ones being specifically tailored for cognition, neurological health, emotional well-being, and psychological improvements, as reflected in the brainwave recordings. Knowing the number of sessions 215 included in the overall treatment profile 142 permits a specialist to optimize the various adjustments occurring between sessions to achieve optimal overall benefits within the planned profile 142.

A qualified or quantified impairment level 220 prior to treatments, during treatments, and post treatments can be recorded. Although shown in aggregate, records may indicate changes on a per treatment basis, in addition to the aggregate course of treatments for a given profile 210. Further, qualitative 225 and quantitative records may be included. In embodiments, although EEG readings are used within sessions, additional tests may be conducted before and after treatment sets to increase fidelity and accuracy of the data sets relied upon. A current gas mixture 230 being utilized for a patient is indicated as is the pressure 235 being applied. In a course of treatments, different sessions can utilize diverse mixture and pressure combinations (adjustments 107) to quantitively determine an optimal treatment regime for a healing state for a given patient (212) and condition (220).

Adjustments (107) may be performed between sessions or within a session. When within a session, a calibration duration 242 to determine optimized settings can be recorded, as can the target (healing state) duration 244, as well as a ramp down 246 time. The total session 248 duration is the sum of these times.

The profile 210 can also record brainwave values observed for the session (in the healing state) or duration 244. These values may be averaged or otherwise grouped (median, mode, mean, etc., standard deviation, for the session. A low and high value within a target range can be established and compared against actual session results. That is values 252-262 can be predicted before a session and confirmed via session captured bio signals to determine a relative success of any given treatment or set of treatments. Values include Delta 252, Theta 254, Alpha 256, Beta 258, Gamma 260, and other. In embodiments, correlations between two or more different values may also be tracked in aggregate, as being indicative of cognitive, neurological, emotional, and/or psychological health. In different embodiments, one or more of the raw values 252-262 may be weighed to bias quotative results for a specific interest. This interest may be based on a cognitive neurological, emotional, and/or psychological condition, a goal of a specific treatment of a set of treatments, or another data-driven factor.

As detailed herein, EEG waveforms may be characterized based on their location, amplitude, frequency, morphology, continuity (rhythmic, intermittent or continuous), synchrony, symmetry, and reactivity. However, the most frequently used method to classify EEG waveforms is by the frequency, so much so, that EEG waves are named based on their frequency range using Greek numerals. The most commonly studied waveforms include Delta (0.5 to 4 Hz); Theta (4 to 7 Hz); Alpha (8 to 12 Hz); and Beta (12 to 30 Hz), Gamma (>30 Hz). In addition, there are other waveforms such as infra slow oscillations (ISO) (less than 0.5 Hz) and high-frequency oscillations (HFOs) (greater than 30 Hz) which are outside the conventional bandwidth of clinical EEG but have recently found clinical importance with the advent of digital signal processing. The frequencies noted for the various types of waves and their ranges are sometimes groups slightly different from what is represented herein and the ranges should be understood to be generalized guides and to not necessarily be strictly construed in all instances.

Alpha (8 to 12 Hz): The posterior dominant alpha rhythm is characteristically present in normal awake EEG recordings in the occipital head region. Alpha brainwaves are slower, and higher in amplitude than Beta ones. A person who has completed a task and sits down to rest is often in an alpha state. A person who takes time out to reflect or meditate is usually in an alpha state. A person who takes a break from a conference and walks in the garden is often in an alpha state. Alpha waves are a defining feature of the normal background rhythm of the adult EEG recording. The posterior rhythm attains the alpha range of 8 Hz at the age of 3 years and does not decline even until the ninth decade of life in healthy individuals. Fast variants of background alpha rhythm are seen in the normal population. Slowing of the background alpha rhythm is considered to be a sign of generalized cerebral dysfunction. The amplitude of alpha rhythm varies in different individuals as well as at different times in the same individual. Reactivity of the alpha rhythm is characteristic and helps in its recognition. It is best seen with the eyes closed and during mental relaxation and is characteristically attenuated by eye-opening and mental effort. In diffuse encephalopathy, patients may portray generalized-alpha activity which is non-reactive to internal or external stimuli and goes by the name of "alpha coma." Mu rhythm is another type of alpha rhythm which presents in the central head regions, and they have an arch like morphology. This rhythm characteristically disappears with the motor activity of the contralateral limbs or thinking about initiating motor activity. However, it is relatively unchanged with eye-opening. They are frequently seen in young adults and are not as common in children and the elderly. Attenuating factors include fatigue, somatosensory stimulation, and mental arithmetic. They are quite asymmetric and asynchronous on the two sides. Females tend to have higher mean frequencies of alpha waves than males. Alpha wave amplitudes are likely to be higher in "outgoing" subjects. Alpha wave amplitudes vary with the subject's attention to mental tasks performed with the eyes closed. In general, amplitudes of alpha waves diminish when subjects open their eyes and are attentive to external stimuli although some subjects trained in relaxation techniques can maintain high alpha amplitudes even with their eyes open.

Beta (12 to 30 Hz): Beta rhythm is the most frequently seen rhythm in normal adults and children. When the brain is aroused and actively engaged in mental activities, it generates beta waves. These beta waves are of relatively low amplitude, and are the fastest of the four different brainwaves. Beta waves are characteristics of a strongly engaged mind. A person in active conversation would be in beta. A debater would be in high beta. A person making a speech, or a teacher, or a talk show host would all be in beta when they are engaged in their work. Beta waves are most prominent in the frontal and central head regions and attenuates as it goes posteriorly. The amplitude of beta activity is usually 10 to 20 microvolts, which seldom increase above 30 microvolts. It often increases in amplitude during drowsiness, NI sleep and subsequently decreases in N2 & N3 sleep. Most of the sedative medications such as barbiturates, chloral hydrate, and benzodiazepines increase the amplitude and quantity of beta activity in individuals. Focal, regional or hemispheric attenuation of beta can occur with a cortical injury, malformations, subdural, epidural or subarea fluid collections. Beta rhythms occur in individuals who are alert and attentive to external stimuli or exert specific mental effort, or paradoxically, beta rhythms also occur during deep sleep, REM (Rapid Eye Movement) sleep when the eyes switch back and forth. Notice that the amplitude of beta rhythms tends to be lower than for alpha rhythms. This does not mean that there is less electrical activity, rather that the "positive" and "negative" activities are starting to counterbalance so that the sum of the electrical activity is less. Thus, instead of getting the wave-like synchronized pattern of alpha waves, desynchronization or alpha block occurs. So, the beta wave represents arousal of the cortex to a higher state of alertness or tension. It may also be associated with "remembering" or retrieving memories.

Delta (0.5 to 4 Hz): Delta rhythm is physiologically seen in deep sleep and is prominent in the frontocentral head regions. Delta rhythm never go down to zero because that would mean that a person was brain dead. Deep dreamless sleep would take a person down to the lowest frequency of delta rhythms. Typically, 2 to 3 cycles a second. When we go to bed and read for a few minutes before attempting sleep, we are likely to be in low beta. When we put the book down, turn off the lights and close our eyes, our brainwaves will descend from beta, to alpha, to theta and finally, when we fall asleep, to delta. Pathological delta rhythm presents in awake states in case of generalized encephalopathy and focal cerebral dysfunction. Frontal intermittent rhythmic delta activity (FIRDA) presents in adults, whereas occipital intermittent rhythmic delta activity (OIRDA) occurs in children. Temporal intermittent rhythmic delta activity (TIRDA) is frequently seen in individuals who have temporal lobe epilepsy.

Theta (4 to 7 Hz): This is the rhythm which is brought on by drowsiness as well as early stages of sleep such as NI and N2. A person who has taken time off from a task and begins to daydream is often in a theta brainwave state. A person who is driving on a freeway, and discovers that they can't recall the last five miles, is often in a theta state—induced by the process of freeway driving. The repetitious nature of that form of driving compared to a country road would differentiate a theta state and a beta state in order to perform the driving task safely. Individuals who do a lot of freeway driving often get good ideas during those periods when they are in theta. Individuals who run outdoors often are in the state of mental relaxation that is slower than alpha and when in theta, they are prone to a flow of ideas. This can also occur in the shower or tub or even while shaving or brushing your hair. It is a state where tasks become so automatic that you can mentally disengage from them. The ideation that can take place during the theta state is often free flow and occurs without censorship or guilt. It is typically a very positive mental state. Theta waves are most prominent in the front-central head regions and slowly migrates backward replacing the alpha rhythm due to early drowsiness. Heightened emotional states can also enhance frontal rhythmic theta rhythm in children and young adults. Focal Theta activity during awake states is suggestive of focal cerebral dysfunction.

Gamma (above 30 Hz) waves are fast oscillations and are usually found during conscious perception. Gamma brainwaves result to simultaneous processing of information from different brain areas. Due to small amplitude and high contamination by muscle artifacts, Gamma waves are underestimated and not widely studied as compared to other slow brain waves. Some have referred to Gamma waves as the most subtle of the brainwave frequencies as the mind has to be quiet to access Gamma. High gamma activity at temporal locations is associated with memory processes. Research studies reported that gamma activity is involved in attention, working memory, and long-term memory processes. Gamma activity is also involved in psychiatric disorders such as schizophrenia, hallucination, Alzheimer's disease, and epilepsy. Gamma waves are highly active when a human experiences states of universal love, altruism, and the 'higher virtues.'

Figure 3:
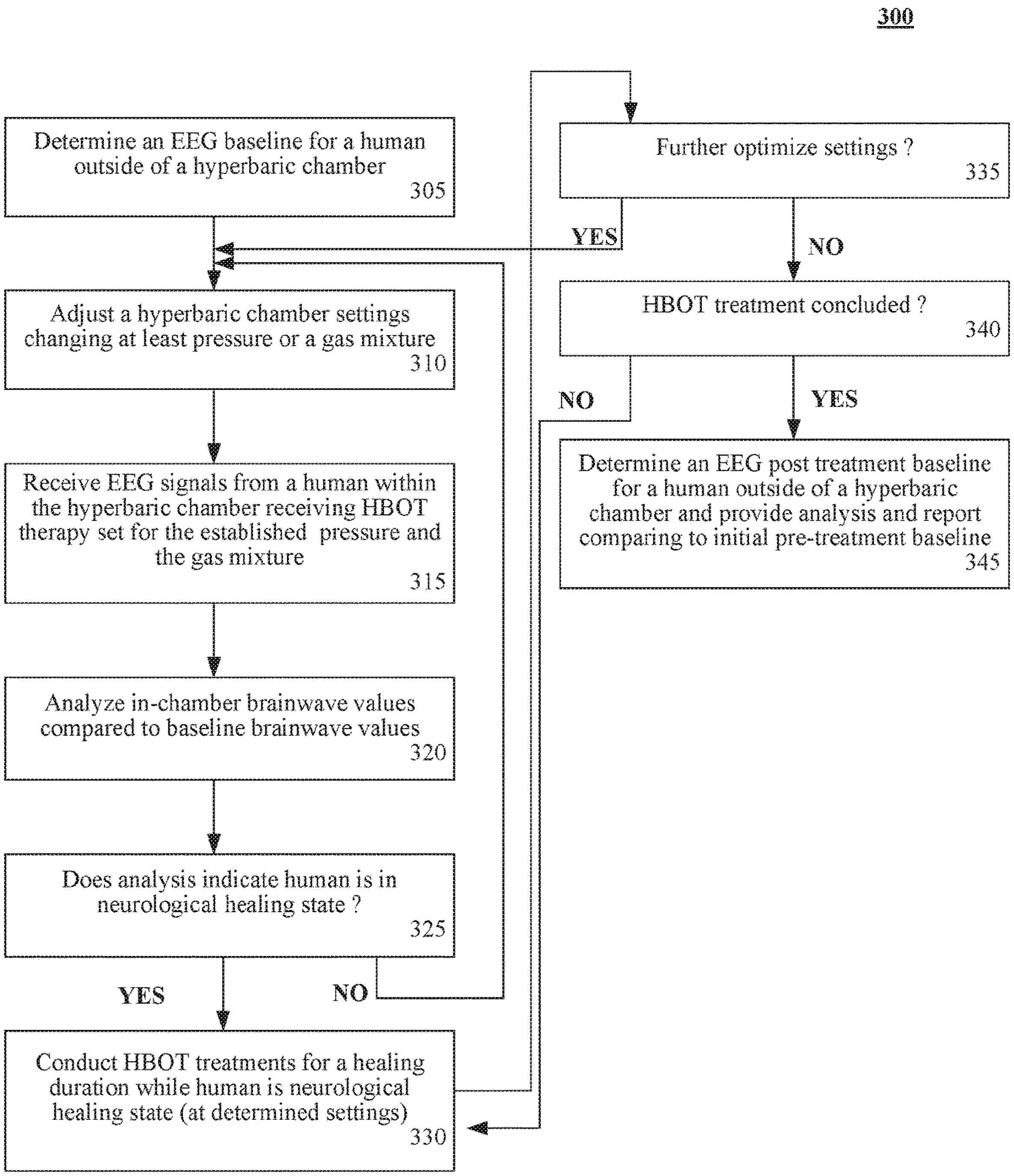
FIG. 3 shows a flow chart of a process for HBOT treatments having brainwave-based adjustments in accordance with embodiments of the disclosure.
Figure 4A:
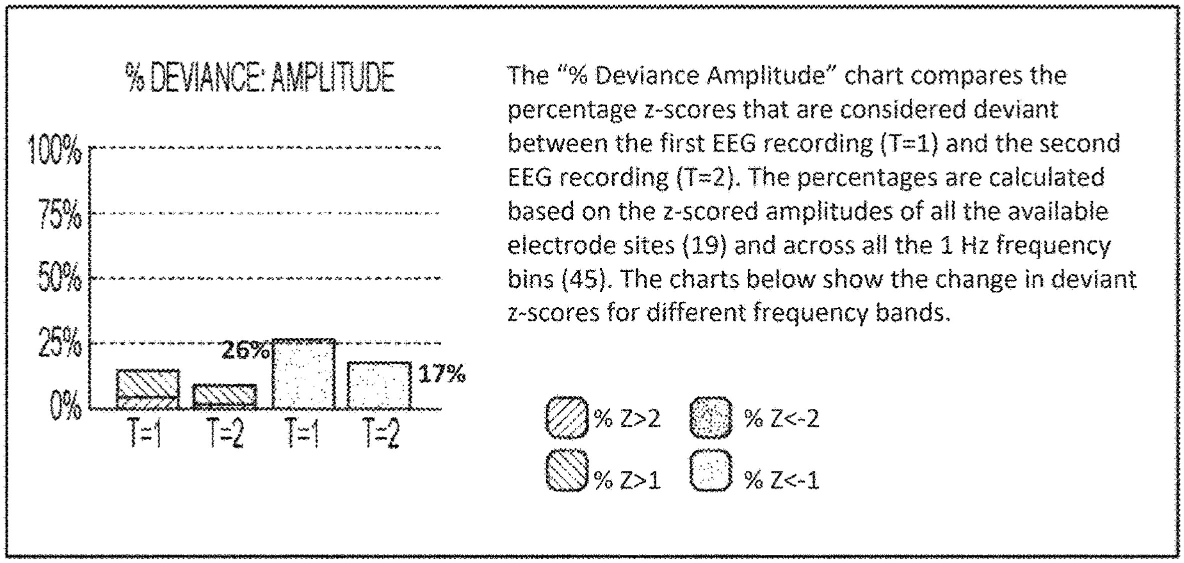
FIGS. 4A, 4B, 4C, and 4D show deviance charts that compare percentage z-scores between different EEG recordings.
Figure 4B:
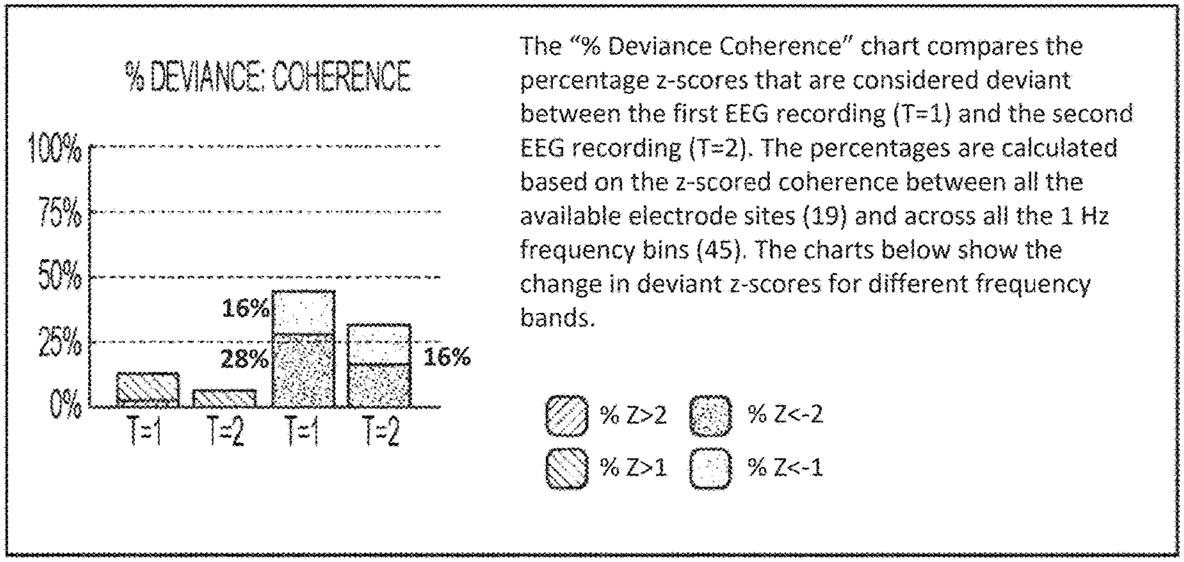
Figure 4C:
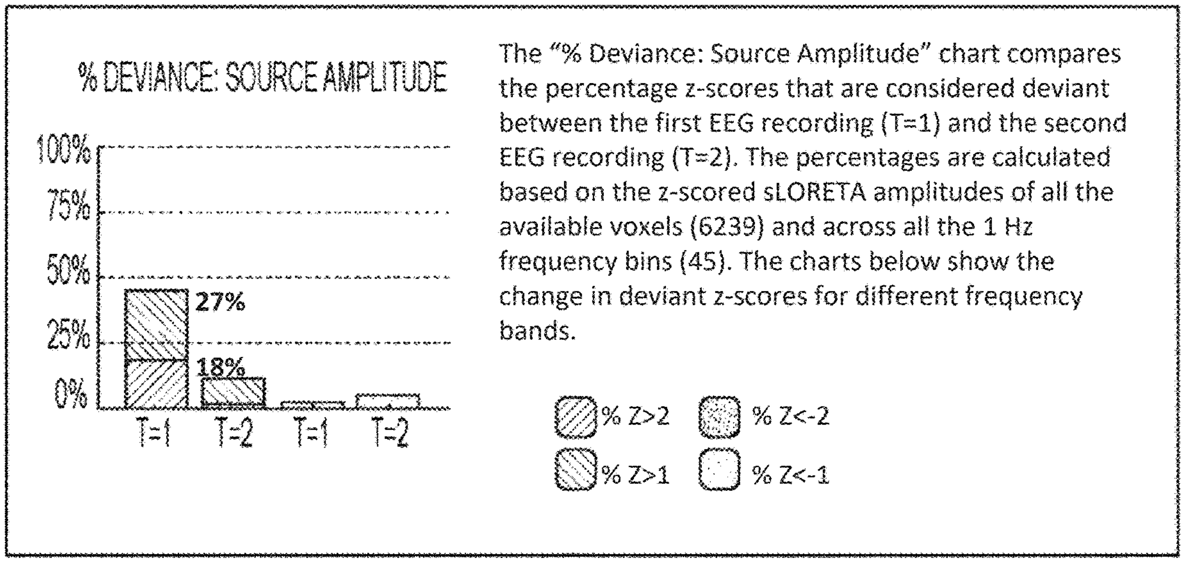
Figure 4D:
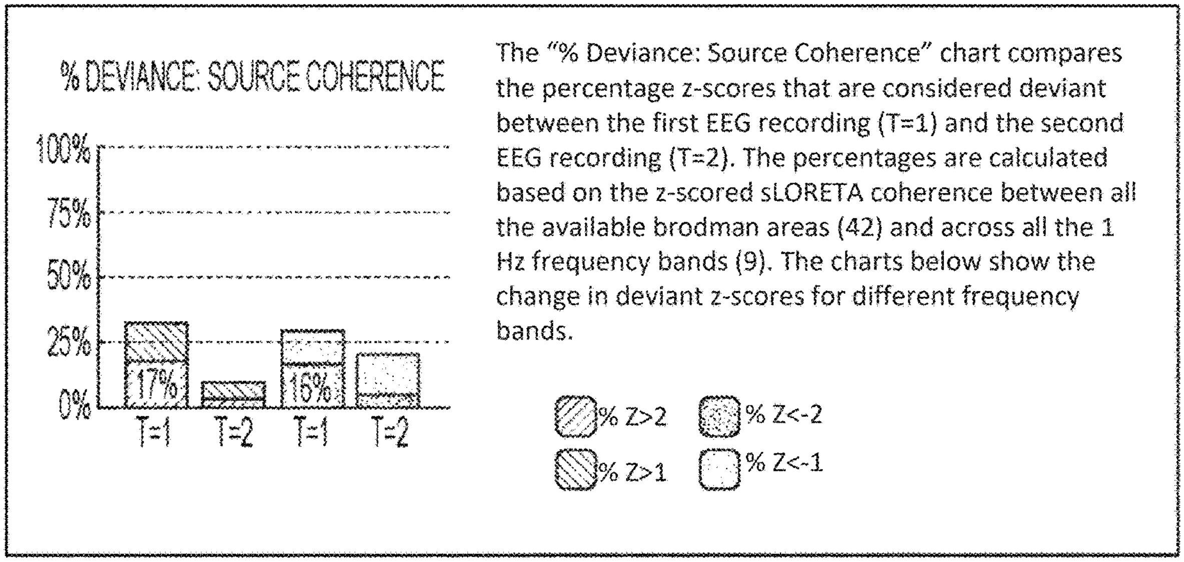

FIG. 3 shows a flow chart of a process 300 for HBOT treatments having brainwave-based adjustments in accordance with embodiments of the disclosure. Process 300 begins in state 305, where an EEG baseline is determined for a human outside a hyperbaric chamber. The human may suffer from cognition, neurological, emotional, and psychological disfunctions, for which HBOT treatments are sought. In other embodiments, the human may not suffer from any disfunctions, but may nonetheless desire HBOT therapy to improve his cognition. A treatment profile 142 can be established, in part based on steps detailed in process 300. After the EEG baseline is acquired, a hyperbaric chamber can be adjusted for settings. This adjustment changes one or more of pressure settings and gas mixture settings. In step 315, EEG signals are received from a human positioned within the hyperbaric chamber that is receiving an HBOT therapy set in accordance with the settings of step 310. From the EEG signals taken while in chamber, under pressure, brainwave values can be analyzed and compared to the baseline brainwave values of step 305.

At this stage (step 325) either an improvement is indicated or not based on the analysis. There are many ways to perform the analysis of the EEG readings, an exhaustive discussion for improvements is well documented in literature and goes beyond the scope of this disclosure. In one embodiment, however, at least two dimensions of improvement (one defined by Alpha and/or Beta EEG values; another defined by Delta and/or Theta values) exists. That is, an overall improvement of cognitive, neurological health, emotional well-being, and/or psychological functions is achieved when one or more Alpha/Beta value improvements is obtained while concurrently improving one or more Delta/Theta values. For purposes of expression and simplicity, the Alpha/Beta values are referred to as "Thought Rhythm values" and Delta/Theta values as Processing Speed values. In reality, each of these are simply different frequencies recorded by an EEG, but a correlation has been found to exist between these pairings and overall improvements. In other words, improvements in Alpha/Beta (Thought Rhythm) at a degradation of Delta/Theta performance (Processing Speed) is not necessarily advantageous. A healing state is defined as being one in which a patent subject to HBOT treatment has appreciable improvements in either or both Thought Rhythm and Processing Speed dimensions, which represents an enhanced overall cognitive state (compared to being outside the chamber). Since brainwaves fluctuate, a sustained difference needs to be quantified between being in and out of chamber. A mathematically sound improvement of at least 5 percent of quantified values taken from both Thought Rhythm and Processing Speed dimensions is determined to qualify for being in a cognitive neurological, and psychological healing state. A more enhanced healing state is achievable with a greater than 5 percent quantified improvement and a positive, but less enhanced healing state is achievable with a lesser than 5 percent (but greater than zero) quantified improvement. Although expressed in mathematical terms, in practice the determination of whether a patient is in a healing state or not may be a subjective call (not an automated one) made by an expert examining EEG values and reports. Similarly, decisions about which (if any) parameters for HBOT therapy should be altered and by what values can be determined or suggested by an automated system based upon data-driven historical information or can be determined by human expertise.

When the human is not in a healing state, settings of the hyperbaric chamber (at least one of gas mixture and pressure) can be adjusted, as expressed from looping from step 325 to step 310. This change can occur within a single HBOT session or across different discrete sessions depending on implementation. If the human is in the healing state as determined form the analysis, the process proceeds from step 325 to step 330. In step 330, the HBOT treatment is conducted for a healing duration while the human is in the cognitive healing state (at the settings established last iteration per step 310). In typical embodiments, the healing duration can be at least 5 minutes and may be significantly longer. Some have, however, noticed improvements from shorter healing durations so shorter healing state durations (such as 1 minute and above) are viable for some treatments. For a 30-minute HBOT session, the healing duration may be 20 minutes. In step 335, a decision as to whether chamber settings should be further optimized or not is made.

If not, the process proceeds to step 340 such that if the HBOT treatment program continues another HBOT treatment is conducted per step 330. If settings are to be further optimized, the process can skip from step 335 to where different chamber settings are established in step 310. If these settings are non-optimal (do not achieve a healing state at least as strong as previous ones), the settings can be readjusted back to the last used ones for which a healing state occurred. If a more optimal healing state is achieved, the new settings can become the default ones.

If a treatment plan is concluded, as determined from step 340, the process can proceed to step 345. In step 345, post treatment EEG readings can be taken for the human outside the hyperbaric chamber. An analysis of the pre treatment state verses the post treatment state can be performed to indicate the positive/negative effects of the treatment in general. Step 345 may be performed at intermediate steps (while HBOT treatments are continuing) in embodiments to receive intermediate baselines. Once a full treatment regime has been conducted, the patient is provided suitable analysis/reports and historical observations can be recorded. In embodiments, past performance of treatment plans can be utilized as training data for expert systems to optimize future iterations per a data driven feedback loop. Over time, repeated effects of treatments (i.e., 40 sessions) can be analyzed to determine if initial improvements repeat, if HBOT improvements diminish with repeated applications, or if HBOT improvements for treated patients accelerate across different treatment courses.

FIGS. 4A-9 show sample reports from a software package called gEEG-Pro. These reports show all major analyses such as Z-scored Amplitude, Phase Coherence, and Alpha Peak detection. Other software packages are able to be adapted and utilized for the EEG processing system 128. Reliance of the gEEG-Pro reporting from actual clinical studies in which aspects of the disclosure are implemented are presented to provide context.

FIGS. 4A, 4B, 4C, and 4D show Deviance charts that compare percentage z-scores between different EEG recordings. Specifically, between a first and second recording. Specifically, differences between two datasets for z-scored amplitudes, z-scored surface coherences, z-scored source amplitudes, and z-scored source coherences are shown based on the sLORETA source construction technique. Changes between the results are indicative of positive results from intervention or treatment, such as the HBOT treatment received. Additional factors, such as time of EEG recordings, sleep quality before recordings, and differences in artifacts of EEG recordings are interpretation considerations. However, by paying attention to these potential result skewing differences and by obtaining multiple different comparisons, a statistically accurate and evidence-based result of improvements resulting from treatments (interventions) is exhibited.

Charts consistent with FIG. 4A-4D are generated for different frequency ranges including Delta (1-3 hz), Theta (4-8 hz), Alpha (8-12 hz), LoBeta (12-15 hz), Beta (15-20 hz), HiBeta (20-30 hz), Gamma (30-35 hz), Alpha1 (8-10 hz), and Alpha2 (10-12 hz).

Figure 5A:
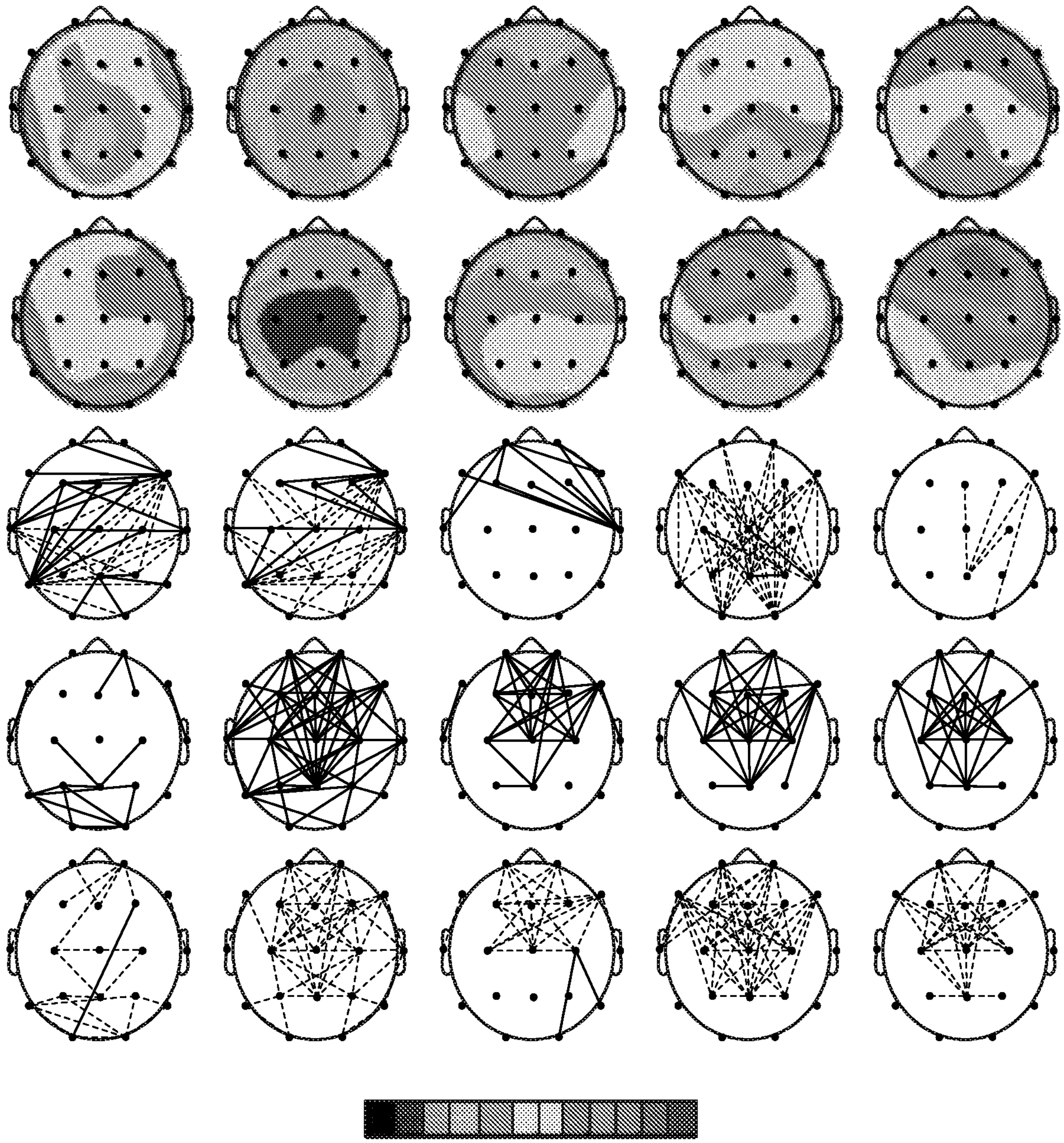
FIG. 5A shows a summary of Z-score analysis across different frequency ranges of an EEG in accordance with embodiments of the disclosure.

FIG. 5A shows a summary of Z-score analysis across different frequency ranges of an EEG in accordance with embodiments of the disclosure. Specifically, the ranges analyzed and visually depicted are Delta, Theta, Alpha, Beta, and Hi Beta. For each, values for absolute power, relative power, amplitude asymmetry, coherence, and phase lag are quantified.

Figure 5B:
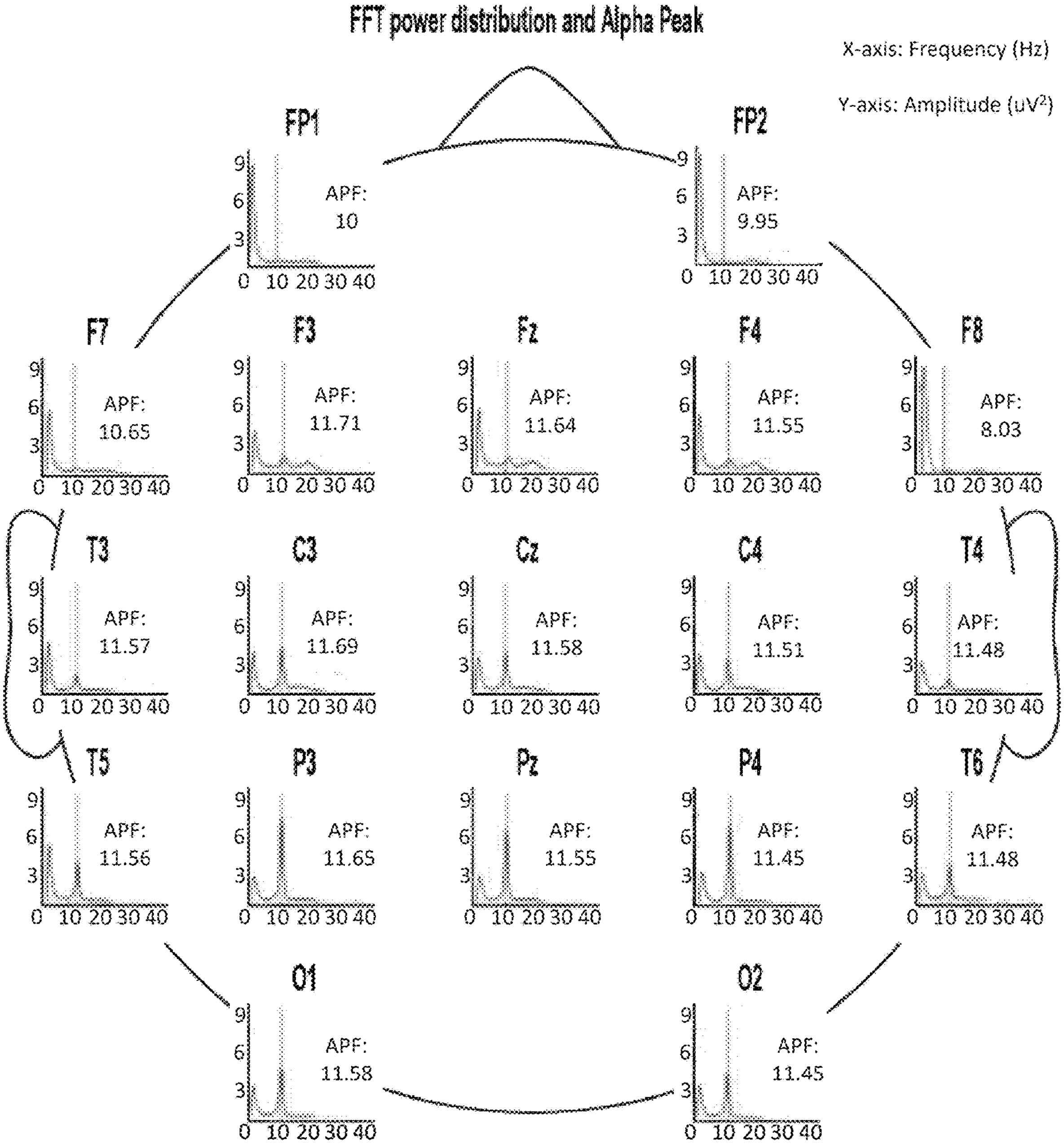
FIG. 5B shows a FFT power distribution and alpha peak report across different frequency ranges of an EEG in accordance with embodiments of the disclosure.

FIG. 5B shows a Fast Fourier Transform (FFT) power distribution and alpha peak report across different frequency ranges of an EEG in accordance with embodiments of the disclosure. As shown 19 different EEG electrodes are shown along with electrode positions and labels. Specifically, a topoplot is depicted showing FFT results for each channel. A red vertical line represents the frequency at which the Alpha Peak Frequency (APF) was detected. The exact peak frequency is expressed to the right of this line.

Figure 6:
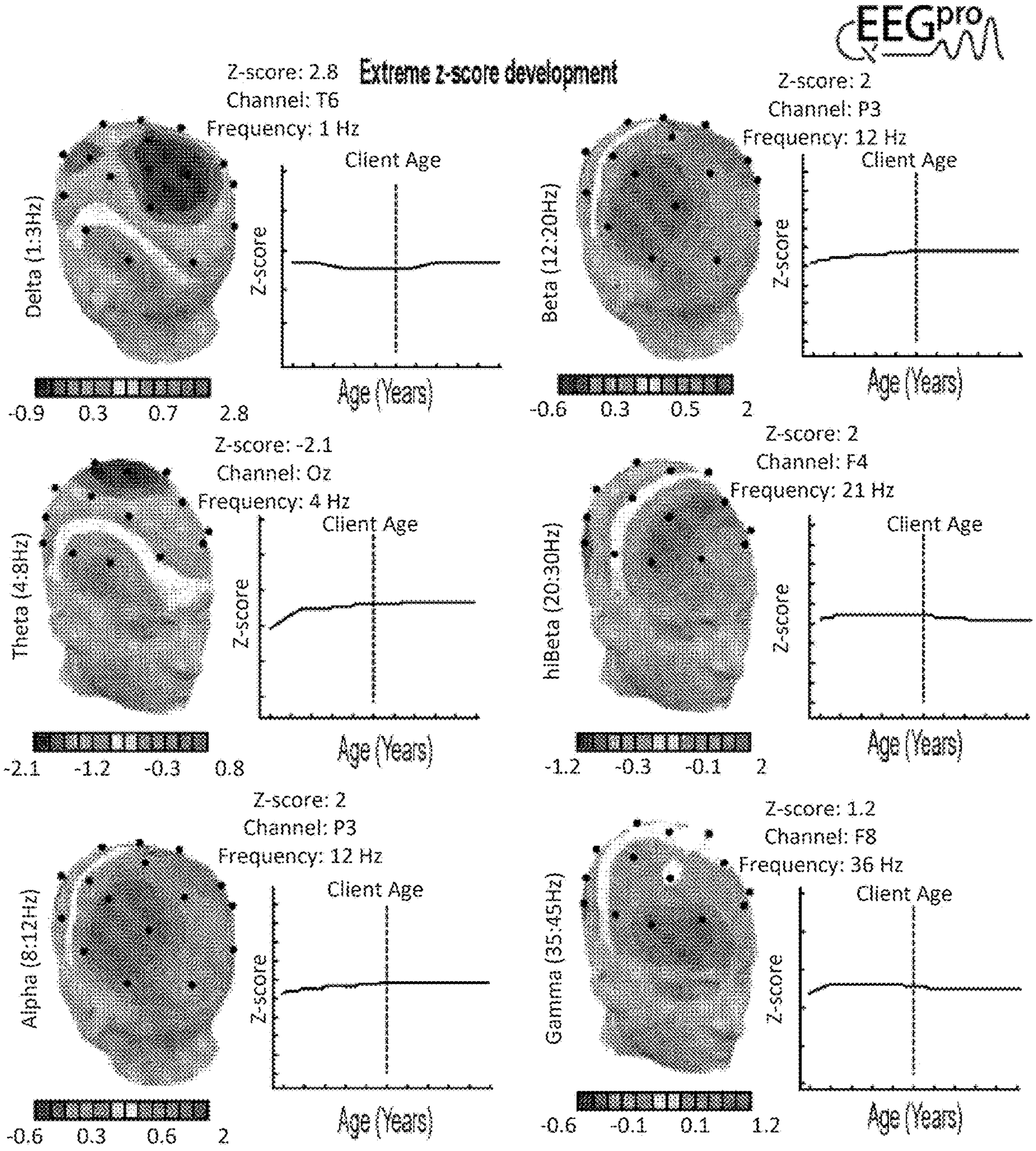
FIG. 6 shows an Extreme Z-Score development report of an EEG in accordance with embodiments of the disclosure.

FIG. 6 shows an Extreme Z-score development report of an EEG in accordance with embodiments of the disclosure. Specifically, for nine frequency bands the frequency is analyzed in which the most extreme Z-score is found. The left panels show headplots which are scaled to the maximum and minimum Z-scores within that frequency. The right panel shows the result of the age simulation analysis. The x-axes of these graphs represent the actual age of the client, marked with a red vertical line, and the simulated ages. The blue line indicates a change in Z-score when the age of the client is artificially changed. This analysis indicates whether the severity of deviant activity that a client shows increases or decreases when the client ages and the EEG stays the same. For example, when a client shows an excess of frontal theta activity at the age of 10 years old, and the Extreme Z-score Development analysis shows that this activity would be less deviant at a younger age and more deviant at an older age, one may conclude that this deviant activity is the result of a maturation lag.

FIG. 7 shows Amplitude absolute power tables and relative power percentages across different EEG frequencies in accordance with embodiments of the disclosure. Specifically, two tables containing the Absolute Power and the Relative power data as well as the Z-scored Absolute and Relative power data respectively. Deviant z-scores are marked in color for quick identification.

FIG. 8 shows a sLORETA summary of different frequencies of an EEG in accordance with embodiments of the disclosure. Specifically, source reconstructions for all discrete frequencies between 1 and 45 Hz for all EEGs in the database are performed using standardized low resolution brain electromagnetic tomography. The sLORETA reports contain results of the Extreme Z-score analysis. For 9 frequency bands the frequency is shown in which the most extreme z-score is found. The left panel shows the transverse, coronal, and sagittal slices (from left to right) of the Montreal Neurological Institute (MNI) template. The voxel that shows the most extreme score is marked with a crosshair. Additionally, functions and symptoms of defects which are associated with specific brain areas are shown. For example, for the parietal lobe and Brodmann area analyzed for Delta readings, defects associated include slow reading, migraines, difficulty with social cues, dyscalcula, denial, receptive language problems, facial recognition problems, and poor social skills. Theta readings are associated with disfunctions of poor comprehension, obsession, focus issues, and impaired spatial perceptions. Alpha readings are associated with problems of impulse, depression, obsessive thoughts of self, and multitasking problems.

FIG. 9 shows scaled summary scores for different frequency ranges based on Z-scores of an EEG in accordance with embodiments of the disclosure. Specifically, the chart shows a percentage of deviant Z-scores in BA40 between 1-8 Hz decreased from 53.1% pretreatment to zero percent post HBOT treatment. The percentage of Z-scores smaller than negative 2 and larger than 2 across a frequency range of 1-30 Hz and across all brain areas decreased from 18.8% pre-HBOT treatment to 0.1% post-HBOT treatment. Accordingly, for this specific case from which the scores were computed, a quantifiable improvement that minimizes deviant brain activity is evident, which results from successful HBOT treatments targeting cognition issues.

The diagrams in the Figures illustrate the architecture, functionality, and operation of possible implementations of systems and methods according to various embodiments of the present invention. It will also be noted that each block of the block diagrams and combinations of blocks in the block diagrams can be implemented by special purpose hardware-based systems that perform the specified functions or acts, or combinations of special purpose hardware and computer instructions.

What is claimed is:

1. A method for performing hyperbaric oxygen therapy (HBOT) comprising:

determining an initial set of Alpha, Beta, Delta, Gamma, and Theta values of a human from electroencephalography (EEG) signals obtained from the human prior to HBOT therapy;

adjusting settings of a hyperbaric chamber to a first pressure and a first gas mixture representing first HBOT settings;

receiving EEG signals obtained from EEG electrodes from the human inside the hyperbaric chamber at the first pressure and at the first gas mixture;

comparing the initial set of Alpha, Beta, Gamma, Delta, and Theta values to a first set of Alpha, Beta, Gamma, Delta, and Theta values obtained from the received EEG signals of the human inside the hyperbaric chamber;

from the comparing, determining whether the human is in a neurological healing state or not, wherein the neurological healing state requires a thought rhythm and speed improvement, wherein the thought rhythm and speed improvement are defined as being at least a five percent improvement quantified by EEG values between the initial set and the first set, wherein the thought rhythm improvement is quantified based on increases in one or more of the Alpha, Beta and Gamma values, wherein the speed improvement is quantified based on decreases of one or more of the Delta and Theta values;

when the human is in the neurological healing state per results of the determining, performing at least one HBOT treatment for a healing duration of at least five minutes at the first pressure and first gas mixture; and when the human is not in the neurological healing state per results of the determining, adjusting at least one of the first pressure and the first gas mixture for the human prior to a subsequent HBOT treatment, wherein the receiving, comparing, determining, performing, and adjusting the at least one of the first pressure and the first gas mixture steps are repeated for a set of HBOT treatments for the human.

2. The method of claim 1, wherein at least 20 HBOT treatments are in the set, for which the adjusting the at least one of the first pressure and the first gas mixture step is performed at least twice.

3. The method of claim 1, wherein at least 40 HBOT treatments are in the set, wherein the method ensures that for at least 20 of the 40 HBOT treatments that the human receiving HBOT treatments experiences quantified cognitive improvements, neurological health improvements, emotional well-being improvements, and/or psychological improvements of a requisite threshold defined by the thought rhythm and speed improvements by being in the healing state for at least the healing duration.

4. The method of claim 3, wherein should values indicative of the cognitive neurological, emotional, and/or psychological improvement fall below the requisite threshold to achieve the healing state for the healing duration, the first HBOT settings are adjusted while performing the at least one HBOT treatment, which affects the Alpha, Beta, Gamma, Delta, and Theta values of the patient to ensure that cognitive improvement is maintained for at least the requisite threshold for the healing state for at least the healing duration.

5. The method of claim 1, wherein the hyperbaric chamber is an enclosure in which the human is exposed to pressure higher than ambient atmospheric pressure, wherein the step of adjusting settings utilizes hyperbaric adjustors for adjusting gas composition within the hyperbaric chamber and for adjusting pressure within the hyperbaric chamber, wherein the EEG signals are indicative of voltage fluctuations resulting from ionic current within neurons of a brain of the human as obtained from EEG electrodes placed along a scalp of the human, wherein the Alpha, Beta, Gamma Delta, and Theta values are determined by an EEG processing system for determining, analyzing, and presenting at least the Alpha, Beta, Gamma Delta, and Theta values of the human.

6. A method for performing hyperbaric oxygen therapy (HBOT) comprising:

determining an initial set of Alpha, Beta, Gamma, Delta, and Theta values of a human from electroencephalography (EEG) signals obtained from a human prior to HBOT therapy;

receiving EEG signals obtained from EEG electrodes from the human inside a hyperbaric chamber at a first pressure and subject to a first gas mixture, said first pressure and said first gas mixture representing first HBOT settings for a first HBOT treatment period;

determining a first set of Alpha, Beta, Gamma, Delta, and Theta values of the human from the EEG signals at the first HBOT settings;

adjusting settings of the hyperbaric chamber to a second pressure and a second gas mixture representing second HBOT settings, wherein the second HBOT settings are different from the first HBOT settings in that at least one of the second pressure and the second gas mixture is different from the first pressure and the first gas mixture;

receiving EEG signals obtained from EEG electrodes from the human inside the hyperbaric chamber at the second pressure and subject to the second gas mixture for a second HBOT treatment period;

determining a second set of Alpha, Beta, Gamma, Delta, and Theta values of the human from the EEG signals at the second HBOT settings; and based on comparisons of the initial set, the first set, and the second set of Alpha, Beta, Gamma, Delta, and Theta values determining which of the initial set, the first set, and the second set quantitatively represents readings for the most favorable quantitative cognitive neurological, emotional, or psychological state for the human;

responsive to a determination that the initial set correlates to the most favorable quantitative cognitive, neurological, emotional or psychological state for the human, recommending that the human not proceed with future HBOT treatments at the first HBOT settings or the second HBOT treatment setting;

responsive to a determination that the first set correlates to the most favorable quantitative cognitive, neurological, emotional, or psychological state for the human, recommending that the human proceed with a set of one or more future HBOT treatments at the first HBOT settings, and proceeding to conduct said one or more future HBOT treatments at the first HBOT settings to quantitively improve a cognitive, neurological, emotional, or psychological state of the human; and responsive to a determination that the second set correlates to the most favorable quantitative cognitive neurological, emotional, or psychological state for the human, recommending that the human proceed with a set of one or more future HBOT treatments at the second HBOT settings, and proceeding to conduct said one or more future HBOT treatments at the second HBOT settings to quantitively improve a cognitive state of the human.

7. The method of claim 6, wherein the first set or the second set correlates to the most favorable quantitative cognitive neurological, emotional, or psychological state, and wherein the first pressure is different from the second pressure.

8. The method of claim 6, wherein the first set or the second set correlates to the most favorable quantitative cognitive neurological, emotional, or psychological state, and wherein the first gas mixture is different from the second gas mixture.

9. The method of claim 6, wherein the first set or the second set correlates to the most favorable quantitative cognitive neurological, emotional, or psychological state, wherein the first pressure is different from the second pressure, and wherein the first gas mixture is different from the second gas mixture.

10. The method of claim 6, wherein the hyperbaric chamber is an enclosure in which the human is exposed to pressure higher than ambient atmospheric pressure, wherein the step of adjusting settings utilizes hyperbaric adjustors for adjusting gas composition within the hyperbaric chamber and for adjusting pressure within the hyperbaric chamber, wherein the EEG signals are indicative of voltage fluctuations resulting from ionic current within neurons of a brain of the human as obtained from EEG electrodes placed along a scalp of the human, wherein the Alpha, Beta, Gamma, Delta, and Theta values are determined by an EEG processing system for determining, analyzing, and presenting at least the Alpha, Beta, Gamma, Delta, and Theta values of the human.

11. The method of claim 6, wherein one or more future HBOT treatments are conducted at the first or second HBOT settings, wherein the one or more future HBOT treatments are conducted for at least a healing duration during which HBOT settings are fixed and during which the human is in a healing state, wherein the healing duration is at least five minutes during which the patient is exposed to higher than ambient atmospheric pressure, wherein the HBOT settings for the future HBOT treatments are expressly calibrated based on brainwave data collected from the EEG signals while the patient was within the hyperbaric chamber, wherein the healing state requires an improvement in the human from the initial settings of a rhythm and speed improvement compared to settings of the HBOT settings of the future HBOT treatments with regard to at least one thought rhythm calibration and at least one thought speed calibration, wherein the rhythm and speed improvement is defined as being at least a five percent improvement quantified by EEG values between the initial settings and the settings of the future HBOT treatments, wherein the thought rhythm calibration is quantified based on one or more of the Alpha, Beta, and Gamma values, wherein the thought speed calibration is quantified based on one or more of the Delta and Theta values, wherein while in the healing state for the healing duration, the EEG signals for the patient are recorded by the EEG system to ensure the patient receiving the HBOT treatment experiences quantified cognitive neurological, emotional, or psychological improvement of a requisite threshold defined by the rhythm and speed improvements for at least the healing duration, wherein should values indicative of the cognitive neurological, emotional, or psychological improvement fall below the requisite threshold to achieve the healing state for the healing duration, the HBOT settings are adjusted, which affects the Alpha, Beta, Gamma, Delta, and Theta values of the patient to ensure that cognitive improvement is maintained for at least the requisite threshold for the healing state for at least the healing duration.

* * * * *